United States Patent [19]

Nappholz et al.

[11] Patent Number: 5,085,215
[45] Date of Patent: Feb. 4, 1992

[54] METABOLIC DEMAND DRIVEN RATE-RESPONSIVE PACEMAKER

[75] Inventors: Tibor A. Nappholz, Englewood, Colo.; Scott Swift, Miami, Fla.; John R. Hamilton; Matthew J. Gani, both of Littleton, Colo.

[73] Assignee: Telectronics Pacing Systems, Inc., Englewood, Colo.

[21] Appl. No.: 497,002

[22] Filed: Mar. 20, 1990

[51] Int. Cl.$^5$ ............................................. A61N 1/368
[52] U.S. Cl. ............................................. 128/419 PG
[58] Field of Search ................................ 128/419 PG

[56] References Cited

U.S. PATENT DOCUMENTS

| | | | |
|---|---|---|---|
| 4,527,568 | 7/1985 | Rickards | 128/419 PG |
| 4,554,921 | 11/1985 | Boute et al. | 128/419 PG |
| 4,624,260 | 11/1986 | Baker, Jr. et al. | 128/419 PG |
| 4,692,719 | 9/1987 | Whigham | 332/11 D |
| 4,702,253 | 10/1987 | Nappholz et al. | 128/419 PG |
| 4,712,555 | 12/1987 | Thornander et al. | 128/419 PG |
| 4,766,901 | 8/1988 | Callaghan | 128/419 PG |
| 4,856,523 | 8/1989 | Sholder et al. | 128/419 PG |
| 4,901,725 | 2/1990 | Nappholz et al. | 128/419 PG |
| 4,932,406 | 6/1990 | Berkovits | 128/419 PG |
| 4,945,909 | 8/1990 | Fearnot et al. | 128/419 PG |

Primary Examiner—William E. Kamm
Assistant Examiner—Kennedy J. Schaetzle
Attorney, Agent, or Firm—Gottlieb, Rackman & Reisman

[57] ABSTRACT

A rate-responsive dual-chamber pacemaker and pacing method for supporting the heart with electrical stimulation at a pacing rate driven by the heart's sinus node or, alternatively, by a sensor adapted to determine the patient's metabolic demand (a metabolic demand indicator). The pacemaker automatically selects between the indicated rates to determine the best pacing rate for appropriately satisfying metabolic demand at all times. The natural rate, driven by the sinus node, takes precedence over the metabolic indicator rate provided the natural rate meets a standard determined by the metabolic demand indicator rate. The pacemaker upper rate response mechanism allows atrioventricular synchrony at natural sinus rates ranging from low rates to high exercise rates, even up to the programmed maximum rate, but maintains ventricular rate stability during pathological atrial tachycardias by reverting to pacing in a rate-responsive VVI mode.

78 Claims, 7 Drawing Sheets

METABOLIC DEMAND DRIVEN RATE-RESPONSIVE PACEMAKER

This invention relates to dual-chamber metabolic demand or rate adaptive (sometimes called rate-responsive) pacemakers and a method of operation and use thereof, and more particularly to such pacemakers which base pacing mode and rate on multiple rate adaptation mechanisms, including atrial synchronous pacing driven by the sinus node and at least one sensor of a physiological parameter to determine metabolic demand. Specifically, the invention concerns improvements in dual-chamber pacing relating to automatic determination of cardiac pacing rate and response to high atrial rates driven by the sinus node.

Physiological pacemakers (the word pacemaker is used herein interchangeably with the word pacer) adapt pacing rate and timing to the patient's needs based on two general schemes: dual-chamber pacing in which intrinsic atrial triggers ventricular pacing, and pacing (single-chamber or dual-chamber) at a ventricular rate related to metabolic demand which is sensed in some manner. Each method of rate adaptation has inherent advantages and disadvantages which a physician must consider in determining the best method for pacing within a diverse patient population.

Dual-chamber pacemakers perform rate adaptation by means of atrial synchronous ventricular pacing where sensing of a natural atrial pulse, called a P wave, activates the process leading to ventricular demand pacing by starting the timing period called the A-V interval. During the A-V interval, the ventricular sense amplifier is capable of sensing a naturally occurring ventricular contraction, or R wave. If the pacer senses an R wave during the A-V interval, a second time period called the V-A interval is immediately started, at the end of which an atrial pulse is generated. If the A-V interval times out before R wave sensing, however, the pacemaker stimulates the ventricle and the V-A interval begins at the end of the A-V interval. This operating mode, characterized by pacing, sensing, and inhibition in both chambers is termed a DDD mode. Atrial synchronous ventricular pacing is best for patients and conditions in which the atrium is normally responsive to metabolic demands since intrinsic stimulation by the sinus node appropriately controls cardiac rate. Pacing in a dual-chamber manner promotes efficient cardiac output by pacing at a natural rate and by maintaining physiological A-V synchrony. DDD pacing is ineffective where an electrically unstable atrium produces frequent extra-systoles, creating intermittent atrial flutter or fibrillation. Another problem inherent in DDD pacing is the retrograde conduction of a stimulus in the ventricle which propagates to the atrium, prematurely stimulating the atrium and triggering the A-V interval, creating a positive feedback loop and resulting in pacemaker-mediated tachycardia (PMT).

Metabolic demand pacemakers, on the other hand, perform rate adaptation using various sensors within the body to measure a parameter related to metabolic demand and to determine a desired pacing rate independent of atrial activity. Recent pacemaker technological advances include a number of accurate physiological sensor mechanisms for determining pacing rate in response to metabolic needs of the body. These metabolic demand pacemakers have clinically proven themselves to properly support the patient's needs. The pacemaker measures a metabolic sensor parameter and, from the parameter, determines a metabolic indicator rate (MIR). In one example of a metabolic demand indicator scheme, changes in minute ventilation, measured using transthoracic impedance, correlate positively to heart rate. Updating cardiac rate relative to the minute ventilation measurement increases pacing rate in a stable but rapid manner, proportional to the level of the workload. Because such pacers do not directly trigger ventricular pacing upon atrial sensing, it follows that these pacemakers do not drive the ventricle in response to unstable upper atrial rate behavior or induce pacemaker mediated tachycardia. However, these pacers do not provide the hemodynamic efficiency inherent in A-V synchronous pacing; in many metabolic pacemakers, the sensor mechanism responds to changing metabolic demand more slowly than a system driven by the sinus node. Also, because a metabolic sensor measures a parameter only secondarily related to cardiac function, extrinsic influences on the sensor may change the heart rate inappropriately.

In a DDD pacemaker, P wave sensing activates the A-V interval delay timer. Following the A-V delay time-out, the pacer stimulates the ventricle. Thus, in a patient having intact cardiac conduction pathways, intrinsic atrial heartbeat sensing may invoke a ventricular pacing rate faster than the pacer's upper rate limit. A pacemaker's upper rate response characteristic defines the way the pacemaker controls the ventricular response to fast atrial rates to prevent ventricular pacing from tracking excessively rapid atrial rates. Present-day DDD pacemakers track intrinsic rate up to a programmed maximum tracking rate where one of three general upper rate behaviors (termed block, fallback and Wenckebach) limits the ventricular pacing rate.

In an atrial based DDD pacemaker the end of the cardiac cycle is defined by P wave sensing of natural atrial depolarization or by time-out and pacing in the absence of timely natural conduction. At this time the pacer sets an A-V delay timer. Upon R wave sensing in the ventricle or following the A-V delay time-out and ventricular pacing, the pacemaker begins timing the postventricular atrial refractory period (PVARP) interval. (In the event of ventricular pacing, the pacer disables atrial sensing and times a short blanking interval to prevent mistaking the depolarization caused by the ventricular pace with natural atrial activity; the PVARP interval begins with the blanking interval, but is much longer.) During the A-V delay and the PVARP intervals, the pacer considers any atrial sensing to be physiologically inappropriate, in some manner not indicative of a proper sinus rate. The A-V delay and the PVARP intervals are consecutive and make up the total atrial refractory period.

In the block upper rate response, the programmed total atrial refractory period (TARP) defines the upper rate limit because the pacer disables atrial sensing during the TARP. If the intrinsic or natural atrial rate increases beyond the upper rate limit, the pacer fails to sense the P waves falling within the TARP and, consequently, does not initiate the A-V delay and ventricular pacing. The upper rate behavior of the pacer depends on the intrinsic atrial rate and the programmed atrial rate limit. When the intrinsic atrial rate is slightly faster than the atrial rate limit, the pacer will not sense P waves in the TARP interval, making the pacer skip ventricular pacing for one of every two atrial heartbeats (2:1 block). As the intrinsic atrial rate increases further, more P waves fall within the TARP, increasing the ratio of atrial to ventricular events, called the degree of the block. A block response characteristically maintains a physiological A-V delay at the expense of the intermittent loss of synchrony as the pacer blocks P wave sensing at fast sinus rates.

Fallback is the second process of ventricular rate slowing in the presence of inappropriate high atrial rates. The fallback upper rate response requires programming of a maximum tracking rate and a fallback rate. The pacer maintains atrioventricular (A-V) synchrony for atrial rates up to the maximum tracking rate. If the intrinsic atrial rate is faster than the maximum tracking rate, the pacer enters ventricular inhibited mode (VVI) by ignoring atrial sensing. In VVI mode, the pacer allows the ventricular rate to gradually fall to the fallback rate in what is termed the fallback response. A pacer using fallback upper rate behavior will track rapid atrial tachycardias, with a 1:1 atrial to ventricular event ratio, up to the maximum tracking rate. A fallback pacer responds to intrinsic atrial rates above the maximum tracking rate by slowing ventricular pacing to the fallback rate, breaking synchrony between atrial and ventricular events for the time the atrial tachycardia remains at a rate higher than the maximum tracking rate. Some pacemakers use the lower rate limit or the programmed minimum rate as the fallback rate. Fallback upper rate response is most appropriate for patients having faulty conduction pathways from the atrium to the ventricle because these patients frequently display pathological atrial rates. In these patients, fallback response effectively limits the rate of ventricular output pulses. However, since fallback response does not maintain A-V synchrony during exercise when a patient most requires the atrial contribution to cardiac output, a fallback pacer fails to satisfy a primary impetus for DDD pacing, maintenance of A-V synchrony under all conditions.

The third process for limiting the upper ventricular rate in dual-chamber pacemakers is the Wenckebach upper rate response. The Wenckebach upper rate process operates in a manner similar to the fallback response. Like the fallback response pacer, the Wenckebach response pacer synchronizes ventricular output pulses to the intrinsic atrial rate until the atrial rate becomes faster than the programmed maximum tracking rate and then paces in the VVI mode by ignoring atrial sensing for intrinsic atrial rates faster than the maximum tracking rate. For intrinsic atrial rates above the maximum tracking rate, the pacer limits the ventricular output rate by setting it to the programmed upper rate limit. The Wenckebach response pacer characteristically prolongs the A-V delay interval progressively for rising intrinsic atrial heart rates because the pacer must wait the time interval defined by the upper rate limit before pacing the ventricle. Eventually, a rising intrinsic atrial heart rate causes a P wave to fall within the PVARP where atrial sensing does not trigger a ventricular pace. For progressively higher intrinsic atrial rates, and depending on the programmed upper rate limit and PVARP duration, the pacer will fail to sense more P waves, increasing the degree of the block (2:1, 3:1, and so on). A Wenckebach pacer, while maintaining A-V synchrony up to higher intrinsic atrial rates than fallback or block pacers, may create nonphysiological A-V delays at atrial tachycardia rates.

Wenckebach response pacers have a further disadvantage, in comparison with block and fallback response pacers, of an increased propensity for initiating pacemaker-mediated tachycardia. In patients having intact retrograde (ventriculoatrial or V-A) conduction pathways, the progressive lengthening of the A-V delay interval may allow the atrial tissue sufficient time to repolarize, resulting in an atrium receptive to depolarization following the ventricular output pulse. If ventricular depolarization causes retrograde conduction of the impulse to the atrium, atrial depolarization may follow; the atrial sense circuitry, in responding, may initiate pacer-mediated tachycardia.

In accordance with the principles of our invention, the pacemaker uses the metabolic indicator rate not only to find an appropriate pacing rate, but also to determine which of the information available to the pacer defines the best pacing rate. The method of pacemaker operation, making rate and operating mode decisions based on the metabolic indicator rate, results in a new upper rate response characteristic, offering improvements and advantages over the prior art block, Wenckebach and fallback modes.

The basic premise of this invention is that both methods for determining cardiac rate, A-V synchronous pacing driven by the sinus node and metabolic demand rate determination, are generally reliable in meeting metabolic needs. A-V synchronous pacing, driven naturally by the sinus node to result in normal, synchronized atrial and ventricular contractions, is the most efficient manner of operation to optimize cardiac output. In the diseased heart, however, atrial tachycardia, bradycardia, unstable physiology or other pathological conditions may exist. The metabolic demand indicator gives rise to a method, independent of sinus node and atrial physiology, for reliably determining metabolic demand and the pacing rate to satisfy that demand. The physiological sensor in the DDDR (DDD with rate response) system of our invention sets limits which indicate when sinus node and atrial physiology is not performing reliably. This allows the pacemaker to detect pathological behavior and respond in a manner to revert the condition, maintaining a stable and appropriate pacing rate despite occurrences of atrial instability.

The pacemaker determines the metabolic indicator rate and uses this rate to vary both the overall pacing rate and the maximum atrial tracking rate (the highest atrial rate for A-V synchrony). By setting the overall pacing rate according to the metabolic indicator rate, the pacemaker determines the lower limit of the cardiac rate when atrial activity is slow or absent. Using the metabolic indicator rate to determine the maximum atrial tracking rate as well allows the pacemaker to respond to exercise in a manner which maintains A-V synchrony all the way up to a programmed maximum rate without switching to a mode comparable to the prior art block, Wenckebach and fallback modes. When the patient exercises, the metabolic indicator rate increases and this elevates the maximum atrial tracking rate. This, in turn, means that as the sinus rate increases with exercise, it is less likely to exceed the maximum atrial tracking rate and the pacemaker can remain in the A-V synchronous mode.

In a sense, the pacemaker of our invention controls pacing rate and mode in an anomalous manner. The metabolic indicator rate has the ultimate control. By varying the maximum atrial tracking rate based on the metabolic indicator rate, the pacemaker determines whether the sinus rate is physiological or pathological. Despite the fact that the metabolic indicator rate is given this ultimate control, however, it is not treated as the best indicator of metabolic needs. As long as the metabolic indicator rate sets the maximum atrial tracking rate greater than the intrinsic atrial rate, the pacing rate is left under the control of the sinus node and atrial conduction physiology, traditional DDD pacing with an atrial beat triggering the A-V delay but with the metabolic indicator rate automatically and continuously determining both the duration of the A-V delay and the cardiac cycle length. The metabolic indicator rate takes control only when the intrinsic atrial rate is too low or too high. If the intrinsic atrial rate is too low, the pacemaker stimulates the atrium at the metabolic indicator rate and stimulates the ventricle after the A-V delay interval, only if it does not sense natural ventricular depolarization during the A-V delay interval. The metabolic indicator rate also takes control, in the VVIR (VVI with rate response) mode, after establishing that the sinus rate is too high. The pacemaker thus gives preference to the sinus rate even though the ultimate arbiter between the rates is the metabolic indicator rate.

While controlling the pacing rate and mode of operation, the pacemaker continuously performs a number of operations. The pacemaker determines both the metabolic indicator rate (MIR) and the natural, or intrinsic, atrial rate (IAR). The pacemaker determines the metabolic indicator rate periodically, at intervals consistent with the method of setting the MIR. For example, the pacemaker may sample the intrathoracic impedance for taking a minute ventilation measurement twenty times per second and update the minute ventilation MIR every 1.6 seconds. Since the sinus node of the heart, together with the atrial conduction pathways, establishes the intrinsic atrial rate, the pacemaker preferably reestablishes the IAR each cardiac cycle. The pacemaker then sets the minimum cardiac pacing rate, the maximum atrial tracking rate, and the VVIR rate based on the MIR. Normally the pacer sets the minimum cardiac pacing rate and the VVIR rate equal or nearly equal to the MIR rate. Occasionally, the pacer may set these control rates to other values to accomplish other purposes such as increasing the rate when attempting to overdrive the natural rate. The pacer sets the maximum atrial tracking rate to a rate based on but faster than the MIR to allow sinus node tracking during exercise or stress.

The pacemaker relates the intrinsic atrial rate to the minimum cardiac pacing rate and the maximum atrial tracking rate. If the IAR is slower than the minimum cardiac pacing rate, the pacer stimulates the atrium and sets the A-V delay in DDDR mode operation. Depending on the metabolic indicator rate, the pacemaker varies the A-A interval as well as the A-V delay. Prior art pacemakers have utilized the metabolic indicator rate to control the overall pacing cycle duration as well as the A-V delay. In the invention, however, the metabolic indicator rate also controls the maximum atrial tracking rate. If the IAR is slower than the maximum atrial tracking rate but faster than the minimum cardiac pacing rate, the pacer senses the natural atrial depolarization and sets the A-V delay to operate in the DDDR mode. If the IAR is faster than the maximum atrial tracking rate, the pacer ignores atrial sensing for purposes of triggering ventricular stimulation and begins operating in the VVIR mode, standard pacemaker VVI but with the rate set to the metabolic indicator rate.

One way in which the pacemaker may relate the intrinsic atrial rate to either the minimum cardiac pacing rate or the maximum atrial tracking rate is to set time intervals within the cardiac cycle wherein P wave sensing before or after an interval boundary corresponds to an intrinsic atrial rate faster than or slower than the comparison rate. The atrial alert period (following the PVARP) is the time interval corresponding to the minimum cardiac pacing rate which, in turn, is normally the most recent value of the metabolic indicator rate. The total atrial refractory period (TARP) is the time interval corresponding to the maximum atrial tracking rate. The pacemaker sets the total atrial refractory period to some percentage of the metabolic indicator rate interval. The value of this percentage is chosen to provide a safe maximum heart rate while the patient is exercising. For the MIR methods described in the illustrative embodiment of the invention the value is a programmable percentage (for example, about 25 percent) of the metabolic indicator rate interval. The pacemaker divides the total atrial refractory period into two subintervals, the A-V delay interval and the PVARP interval, both of which are based on the reciprocal of the MIR. In this manner the pacemaker increases maximum atrial tracking rate with exercise by decreasing the PVARP. Following every ventricular beat there is a PVARP during which the pacemaker should not sense P waves. (For a blanking interval following ventricular stimulus generation, the pacer blanks the atrial sense amplifier to ignore atrial signals. The duration of the blanking interval varies depending on the pace delivery configuration of the pacemaker, for example, depending on whether sensing is unipolar or bipolar or whether charge balancing of the pacing pulse is selected. A common duration for the blanking interval is about 80 milliseconds. It is impossible to sense reliably in the aftermath of a ventricular stimulus. But the PVARP is much longer than 80 ms.) If the pacer senses a P wave during the PVARP, the atria are beating too rapidly. This is because the PVARP is the interval immediately following the preceding A-V delay interval, so any P wave occurring during the PVARP is too close to the preceding atrial beat. A P wave falling subsequent to the PVARP has a rate lower than the maximum atrial tracking rate. It is slow enough to be considered nonpathological, so the pacemaker responds by triggering ventricular pacing in A-V synchrony (DDD pacing). P waves falling during the PVARP control a switch from the DDD mode to the VVI mode. In VVI operation, ventricular pacing occurs without reference to the sensing of atrial beats. By using the metabolic indicator rate to decrease the PVARP during exercise, the atrial beats occurring more rapidly as the sinus rhythm increases are now less likely to fall in the PVARP. Consequently, by having the metabolic indicator rate control the PVARP, the metabolic indicator rate is able to extend the DDD mode of operation during periods of even heavy exercise.

Both the PVARP and the A-V delay intervals depend on the instantaneous value of the metabolic indicator rate. As stated, the sum of the A-V delay and the PVARP define the maximum atrial tracking rate. The A-V delay varies inversely with metabolic indicator rate to promote A-V synchrony when exercising. A pacemaker performs its most efficient cardiac operation to maximize cardiac output when the A-V delay interval is set to generally correspond to normal A-V intervals occurring naturally, resulting in normal, synchronized atrial and ventricular contractions. When the cardiac rate changes according to metabolic demand, the pacer improves the efficiency of cardiac function by automatically varying the A-V delay in a physiological manner to allow optimum filling time for the ventricles. The pacer automatically shortens the A-V delay interval for faster metabolic indicator rates. For patients having sinus node dysfunction, a standard DDD pacing system will not set ventricular pacing rate to correctly respond to variations in metabolic demand. Metabolic indicator sensing provides rate responsiveness under this condition as well as when atrial sensing disappears for technical reasons (for example, changes in sensitivity over time). For instances of electrical instability of the atrium or an atrium which does not respond to increased metabolic demand, the invention detects insufficient atrial functioning and automatically switches to a pacing rate driven by metabolic demand.

The pacemaker switches operation from the DDDR to the VVIR mode when the intrinsic atrial rate is faster than the atrial tracking rate. In the illustrative embodiment of the invention, the pacemaker switches to the VVIR mode when P waves fall within the PVARP interval for a predetermined number of consecutive cardiac cycles (for example, two cardiac cycles). (The intrinsic atrial rate corresponds to the time interval between the last P wave and the present one, and the rate is too fast because the corresponding time interval is shorter than the total atrial refractory period.) An alternative example of a mechanism for switching operation from the DDDR mode to the VVIR mode is to switch modes when the intrinsic atrial rate is faster than the maximum atrial tracking rate in a predetermined percentage of the most recent cardiac cycles (for example, when four of the last eight P waves arrive too frequently).

There must also be some mechanism for the pacer to switch back to the DDDR pacing mode upon atrial rate slowing. A device called the atrial activity monitor is the means used by the illustrative embodiment of the invention for returning to the DDDR pacing mode in our pacemaker. In the VVIR mode, the pacemaker continues to detect the intrinsic atrial rate to determine whether it remains faster than the maximum atrial tracking rate. During VVIR pacing, the metabolic indicator rate continues to control the TARP interval duration and, consequently, the setting of the maximum atrial tracking rate. Atrial sensing continues even though the sensing of a P wave in no way influences the generation of ventricular pacing pulses, the only pacing pulses which are being generated while operating in this mode. In general, the atrial activity monitor will update and store a representation of the number of consecutive cardiac cycles or the percentage of cardiac cycles having an intrinsic atrial rate slower than the maximum atrial tracking rate for a short period of time (defined by cardiac cycles or by a timer). The atrial activity monitor updates and stores the recent history of atrial activity while operating in the VVIR mode in response to a high intrinsic atrial rate. The atrial rate monitor may also update and store a history of atrial activity according to the stability of the recent intrinsic atrial rates. If intrinsic atrial rates vary too much from a prescribed criterion, the pacer may prevent a return to the DDDR mode regardless of the magnitude of the rates. When the atrial activity history meets some criterion for returning to the DDDR mode, the atrial activity monitor restores DDDR pacing. This criterion preferably allows the pacer to return to DDDR pacing quickly in response to a premature atrial contraction but to slowly assume DDDR pacing after an episode of atrial tachycardia.

In the illustrative embodiment of the invention, the pacer continues sensing P waves and determines whether the time between consecutive P waves, the P-P interval, is longer or shorter than the TARP while operating in the VVIR mode. IF a P-P interval is shorter than the TARP the intrinsic atrial rate is too high to safely return to A-V synchronous pacing. When P-P intervals become longer than the TARP the intrinsic atrial rate does not indicate the presence of pathological atrial tachycardia and the pacer may consider returning to DDDR mode pacing. The pacer only senses these P waves to determine whether it can switch back to the DDDR mode. It is not enough, however, for a single P-P interval to be longer than the TARP. Instead, the switch back to the DDDR mode depends on how long the pacemaker has been operating in the VVIR mode. The longer the sinus rate has not been used to drive the pacemaker, the more rigorous the test which must be passed to revert back to reliance on the sinus rhythm. In this implementation of the pacemaker, the atrial activity monitor is a counter which is incremented for each P-P interval which is shorter than the TARP and decremented for all P-P intervals longer than TARP. The maximum count of the counter is three. The VVIR mode begins when the pacer is operating in the DDDR mode and senses P waves within the PVARP for a preset number of consecutive cardiac cycles. The pacemaker increments the atrial activity monitor counter from zero to one and continues to operate in the DDDR mode until consecutive cycles with premature P waves meet the preset number and the pacemaker switches its operating mode from DDDR to VVIR. At this time the atrial activity monitor will have incremented or decremented its count in each cardiac cycle depending on whether P waves fell within PVARP. The atrial activity monitor count and the timing of subsequent P wave sensing will determine how long the pacemaker remains in VVIR mode. So long as the atrial activity monitor count is greater than zero, the pacemaker will function in the VVIR mode. If the next P-P intervals are longer than the TARP for a number of cardiac cycles equal to the atrial activity monitor count, the pacer decrements the atrial activity monitor counter back to zero and returns to operating in the DDDR mode in the next cardiac cycle. However, if several P-P intervals are shorter than the TARP, or more accurately if more P-P intervals are shorter than TARP than are longer, the pacer increments the atrial activity monitor counter up to a maximum of three. This requires a sequence during which there are three more P-P intervals longer than TARP than P-P intervals shorter than TARP before the pacer decrements the counter back to zero and switches to the DDDR mode.

When the pacer detects an elevated atrial rate and responds by reverting to the VVIR pacing mode, pacing and sensing in the ventricle is no longer synchronized to natural atrial activity. The pacemaker continually updates TARP timing based on metabolic indicator rate, thereby retaining the mechanism for determining when the intrinsic rate of P waves is sufficiently slow to allow the pacer to return to DDDR pacing. When the pacer is generating stimulating pulses in the ventricle and the patient has intact retrograde (V-A) conduction pathways, the depolarizations in the atrium may not be P waves driven by the sinus node but rather retrograde depolarizations triggered by pacemaker-generated ventricular pulses. These retrograde depolarizations during the VVIR mode can cause atrial P wave sensing to continually fall within the PVARP interval, locking the pacer into the VVIR mode, even though the actual time intervals between successive P waves are long enough so as not to indicate the presence of tachycardia. We call this phenomenon pacemaker-mediated VVIR operation (PMVVIR).

The pacemaker uses a retrograde monitor to detect and terminate the PMVVIR condition. The retrograde monitor, like the atrial activity monitor senses P waves and correlates P wave timing within the cardiac cylcle with time intervals (PVARP and TARP) determined from the metabolic indicator rate. The atrial activity monitor correlates the interval between P waves with the duration of the TARP to determine rate information. The retrograde monitor does the same but also correlates P wave timing with the PVARP interval within the cardiac cycle. The atrial activity monitor determines whether the atrium is driving the heart too fast. The retrograde monitor detects when the ventricle and atrium are acting in synchrony but with the ventricle driving the atrium. When the pacer senses an atrial depolarization event during the PVARP while operating in the VVIR mode, this event may be either a P wave occurring at a tachycardia rate or a retrograde depolarization. The pacemaker distinguishes these phenomena by measuring the time between this and the previous atrial sensed event. This time duration is the P-P interval. If the P-P interval (or a running average of the P-P interval) is greater than the interval corresponding to the maximum atrial tracking rate, the depolarization may well be a retrograde P wave. However, it may not be. During VVIR operation the pacemaker cannot be certain that the rate is sufficiently slow (the P-P interval sufficiently long) to indicate an absence of atrial tachycardia, since the pacer will fail to detect a P wave occurring during atrial blanking in the cardiac cycle (i.e., the measured P-P interval may in fact represent two short intervals rather than one long interval). Due to this uncertainty, the pacemaker requires a statistical measure to better determine whether P waves arise from retrograde conduction. The retrograde monitor performs this statistical analysis.

The retrograde monitor updates and stores the recent history of cardiac cycles showing the PMVVIR characteristic, a P wave falling within the PVARP but having a P-P rate slower than the maximum atrial tracking rate. When the retrograde history meets some statistical criterion indicating the presence of PMVVIR, the pacemaker sets into action a mechanism for terminating the condition. To determine the presence of PMVVIR, the retrograde monitor counts consecutive cycles having the PMVVIR characteristic (a P wave during the PVARP interval and a P-P interval at a nontachycardia rate) rather than a predominant number of cycles because a single cycle with atrial activity at a tachycardia rate implies that a preceding PMVVIR cycle failed to detect a high rate P wave due to blanking. The number of consecutive PMVVIR cyles triggering the terminating mechanism balances considerations of false PMVVIR detection (for too few cycles) against discomfort to the patient inherent in allowing the PMVVIR condition to persist. The range of consecutive cardiac cycles from three to eight, five in the illustrative embodiment of the invention, appropriately define a PMVVIR episode. A single cycle in which the PMVVIR characteristic is not detected results in resetting of the retrograde monitor count.

Upon detecting PMVVIR, the pacemaker terminates it using a pacing cycle extension mechanism wherein the pacer ignores subsequent P waves falling in the PVARP interval and extends the atrial cycle timer, in just the present cycle, by a time interval (200 to 300 ms) sufficient to best allow the atrium to recover from the retrograde depolarization and re-establish A-V synchrony. Retrograde depolarization may cause the atrium to enter a refractory state in which natural activity in response to sinus node stimulation will not initiate natural depolarization. By extending the atrial cycle length, the pacemaker allows time for the atrium to recover and respond naturally to the sinus node to restore A-V synchrony. Together with extending the cycle, the pacemaker resets the retrograde monitor.

BRIEF DESCRIPTION OF THE DRAWINGS

Further objects, features and advantages of our invention will become apparent upon consideration of the following detailed description in conjunction with the drawings, in which.

DETAILED DESCRIPTION

Figure 2:
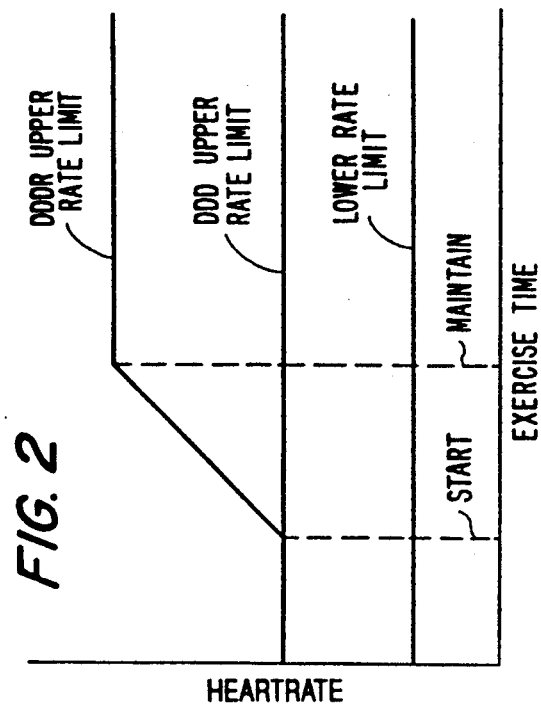
FIG. 2 is a graph of the exercise response of the pacemaker as compared to the exercise response of a prior art DDD pacemaker in response to linearly increasing stress due to exercise, and shows the improvement in atrial tracking ability.

There is a considerable body of prior art in dual-chamber pacemaker systems which automatically select the pacing mode of operation on a cycle by cycle basis by enabling or disabling atrial and ventricular pacing and sensing. The use of an external programmer to communicate with an implanted pacemaker is also well known. Specific reference may be made of U.S. Pat. No. 4,766,901, describing the operation of a rate-responsive pacing system using the integrated evoked potential for a metabolic demand pacing rate indicator. U.S. Pat. No. 4,702,253 discloses a rate-responsive pacemaker describing a second metabolic demand pacing rate indicator, respiratory minute volume, as the rate control parameter. U.S. Pat. No. 4,692,719 describes electronic circuitry capable of performing electrocardiogram sensing for analyzing intrinsic and evoked potential cardiac signals. Improved pacemakers are disclosed in Callaghan et al. Application Ser. No. 173,573 entitled "Rate-Responsive Pacemaker with Closed-Loop Control", filed on Mar. 25, 1988, and Nappholz et al. U.S. Pat. No. 4,901,725 entitled "Minute Volume Rate-Responsive Pacemaker". The aforementioned patents, are hereby incorporated by reference.

A metabolic sensing system suitable for the present invention could be made up of one or more of various sensing mechanisms, including but not limited to minute volume, depolarization gradient of the evoked potential, QT-interval, oxygen saturation, pH, central venous blood temperature, right ventricular pressure, stroke volume, systolic time intervals, respiration rate, and ultrasound. The method and apparatus of our invention will work with any metabolic indicator system able to reliably relate the sensor parameter to metabolic demand pacing rate. Preferred embodiments include either minute volume, integrated evoked potential, or both in a dual sensor system. Telemetry between an external programmer and the pacemaker may activate or deactivate a sensor system or control the influence of both sensors in a dual sensor system. The combination of minute volume and evoked potential sensor systems does not require additional sensing leads over the number required for a DDD system alone.

The prior art teaches the use of a controller, which may be a microprocessor, to govern operation of an implantable apparatus for delivering stimulus pulses to cardiac tissue. The controller initializes, activates, inhibits, and responds to at least one timer circuit, as well as circuitry for sensing external events in at least one cardiac channel. A detailed understanding of these operations is well known in the art.

U.S. Pat. No. 4,702,253 teaches a means for determining a metabolic indicator rate (MIR) interval from a minute volume measurement. The minute volume measurement and pacing rate interval determination take place independently of and asynchronously to the cardiac cycle discussed below. The MIR mechanism may communicate its result, the MIR rate parameter, to the pacemaker control circuitry through storage in random access memory which the control circuitry accesses at appropriate times.

U.S. Pat. No. 4,766,901 discloses a system for measuring integrated evoked potential, deriving from it a depolarization gradient, and determining a metabolic indicator rate from the result. The evoked potential measurement and rate determination take place as part of a cardiac cycle, but how this is accomplished is described in the prior art. The present invention disclosure treats the evoked potential measurement and rate determination as a "black box" subroutine called by the pacemaker within the flow of invention operations. The evoked potential rate-determining means may communicate its MIR parameter to the pacemaker control circuitry through storage in random access memory which the control circuitry accesses at appropriate times in a cardiac cycle.

A pacemaker functions continuously on a cardiac cycle by cycle basis. All operations comprising the method and apparatus of our invention take place within this cyclical framework. The pacemaker determines the metabolic indicator rate periodically, at intervals consistent with the method of determining the MIR. Of the two types of metabolic indicator rate determining methods discussed here, the evoked potential MIR has a cardiac cycle basis and the minute volume MIR does not. Since the nature and type of metabolic indicator rate determining method is not of importance to the subject invention, this invention description assumes that the MIR parameter is continuously available to the pacemaker at all times.

The pacemaker first determines the metabolic indicator rate (MIR) and, for each cardiac cycle, determines from it operational rates or intervals. For a given implementation, the metabolic indicator rate determining method may supply the pacemaker with the metabolic indicator rate or its reciprocal, the metabolic indicator rate interval. From either of these MIR parameter values, the pacer will determine requisite rates or intervals. The pacemaker uses the MIR parameter to determine (a) the minimum cardiac pacing rate, (b) the maximum atrial tracking rate, and (c) the ventricular pacing rate.

(a) The minimum cardiac pacing rate is the overall DDDR pacing rate, the lower limit of the cardiac rate when atrial activity is slow or absent. In the illustrative embodiment of the invention, the pacemaker sets the minimum cardiac pacing rate equal to the MIR rate.

Figure 1:
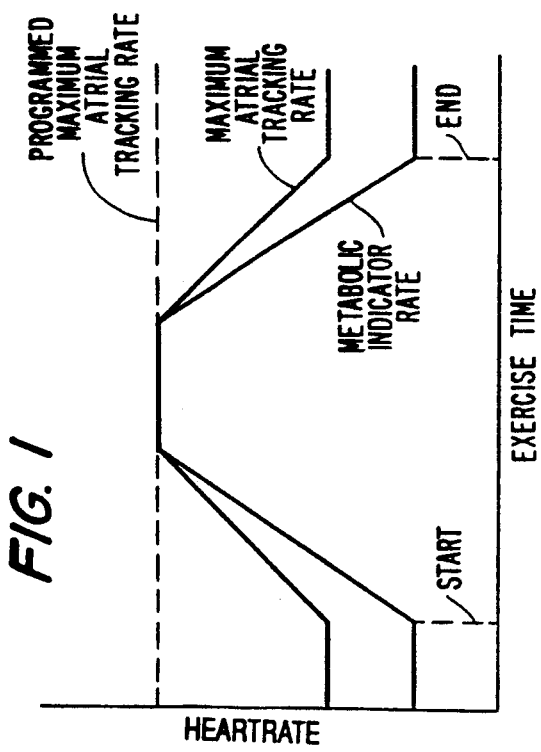
FIG. 1 is a graph of the exercise response of the pacemaker of the illustrative embodiment of our invention in terms of the instantaneous heart rate for linearly increasing stress due to exercise and linearly decreasing stress when exercise ends, and illustrates how the pacemaker determines maximum atrial tracking rate from metabolic indicator rate while the patient is exercising.

(b) The maximum atrial tracking rate is the highest intrinsic atrial rate for which the ventricle is paced in synchrony with natural atrial activity. The pacer sets the maximum atrial tracking rate to a rate proportional to and higher than the MIR to allow sinus node tracking during exercise or stress. The relationship for determining maximum atrial tracking rate from the metabolic indicator rate is based on a clinical evaluation of the particular metabolic indicator method and how the derived MIR relates to the upper limit on pacing rate for an exercising patient. By basing the maximum atrial tracking rate on the MIR, when the patient exercises the metabolic indicator rate increases and this elevates the maximum atrial tracking rate. This, in turn, means that as the sinus rate increases with exercise, it is less likely to exceed the maximum atrial tracking rate and the pacemaker can remain in the A-V synchronous mode. FIG. 1 illustrates a typical relationship between the metabolic indicator rate and the maximum atrial tracking rate. The pacemaker maintains A-V synchrony from low intrinsic atrial rates all the way to the programmed maximum atrial tracking rate during exercise so long as the intrinsic rate does not exceed the maximum atrial tracking rate. FIG. 2 compares the exercise response of a standard DDD pacemaker with that of the present invention. Because the DDD upper rate limit does not change in response to exercise, a DDD pacer will maintain A-V synchrony only to a level considered safe for a resting patient. During exercise, the DDD pacer will start its upper rate response at a much lower intrinsic atrial rate, defeating A-V synchrony when its efficiency is most needed.

(c) The ventricular pacing rate is the cardiac pacing rate for the ventricle when high atrial tachycardia rates cause the pacemaker to shift from the DDDR to the VVIR mode. In the illustrative embodiment of the invention, the ventricular pacing rate in the VVIR mode is the same as the minimum cardiac pacing rate in the DDDR mode.

The pacemaker determines the metabolic indicator parameter and establishes the operational pacing rates; also, during each cycle it senses natural atrial activity for the purposes of measuring the intrinsic atrial rate. The pacemaker compares the intrinsic atrial rate to the maximum atrial tracking rate to determine the mode and pacing rate for that, and possibly other, cardiac cycles.

The manner of determining the relationship between the intrinsic atrial rate and either the minimum cardiac pacing rate and the maximum atrial tracking rate is to set time intervals within each cardiac cycle. P wave sensing before or after an interval boundary corresponds to an intrinsic atrial rate faster than or slower than the comparison rate.

Figure 3B:
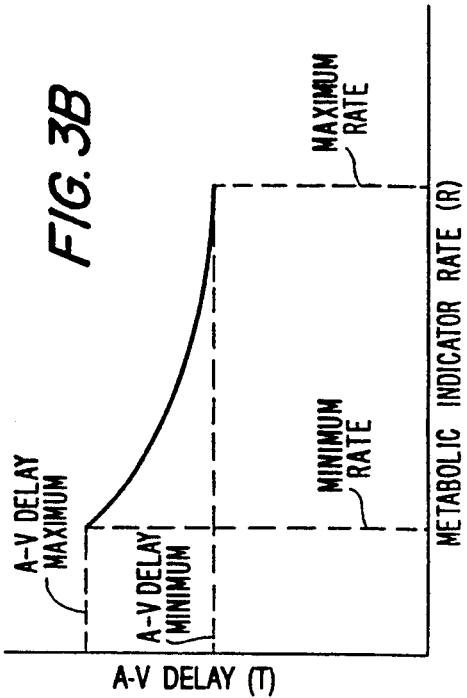
FIGS. 3A and 3B set forth graphic representations of the mechanism for automatically determining a rate adaptable A-V delay interval from the metabolic indicator rate, in terms of cardiac cycle time and rate, respectively.
Figure 3A:
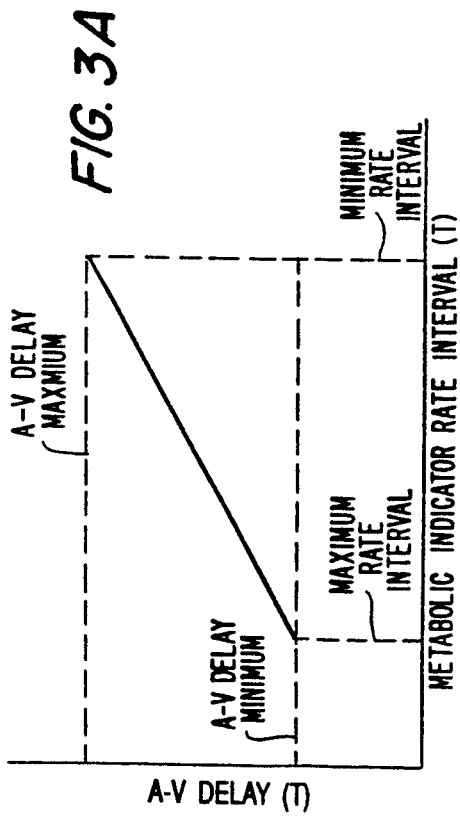

The A-V delay is one of the intervals necessary for DDD pacing. At the end of the atrial cardiac cycle, on time-out of the A-A interval timer or upon atrial sensing of an intrinsic atrial rate slower than the maximum atrial tracking rate, the pacemaker sets a timer to the A-V delay value. When the timer expires, unless pacing is inhibited by ventricular sensing prior to time-out, the pacemaker generates a stimulating pulse in the ventricle. In our invention, the pacemaker varies the A-V delay interval in a manner inversely proportional to the metabolic indicator rate. FIGS. 3A and 3B illustrate the manner of determining the A-V delay from the metabolic indicator rate or the metabolic indicator rate interval. In the illustrative embodiment of the invention, the A-V delay for the current metabolic indicator rate or rate interval is determined by linearly interpolating between two points. In FIG. 3A, one point is defined by predetermined values of minimum rate interval and A-V delay maximum, the other by maximum rate interval and A-V delay minimum. In FIG. 3B, the A-V delay determination is shown in terms of metabolic indicator rate.

Figure 5A:
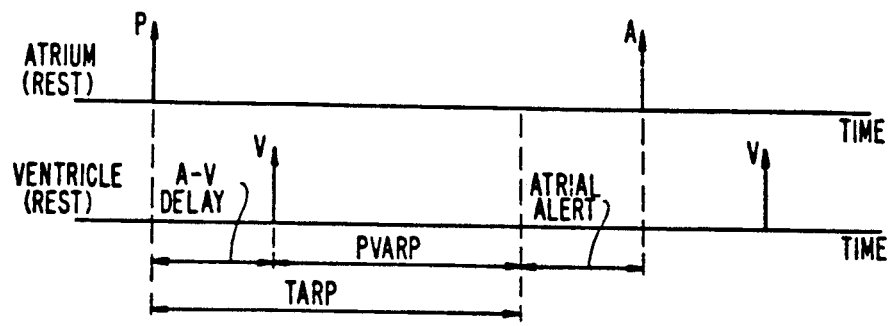
FIGS. 5A and 5B are timing diagrams of two cardiac cycles and their associated timed intervals.
Figure 5B:
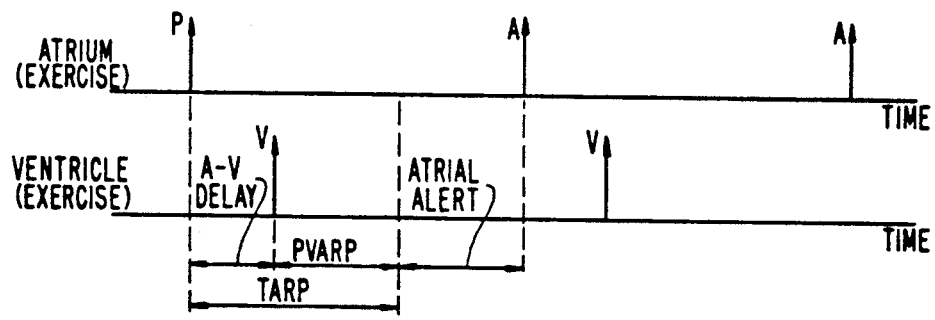

Referring to the cardiac cycle timing diagram in FIGS. 5A and 5B, the A-V delay interval becomes shorter in the presence of an exercise-induced acceleration of metabolic indicator rate. Changing the A-V delay inversely with respect to metabolic indicator rate promotes A-V synchrony when exercising. The pacer automatically shortens the A-V delay interval for faster metabolic indicator rates and increasing physiological intrinsic atrial rates.

Figure 4A:
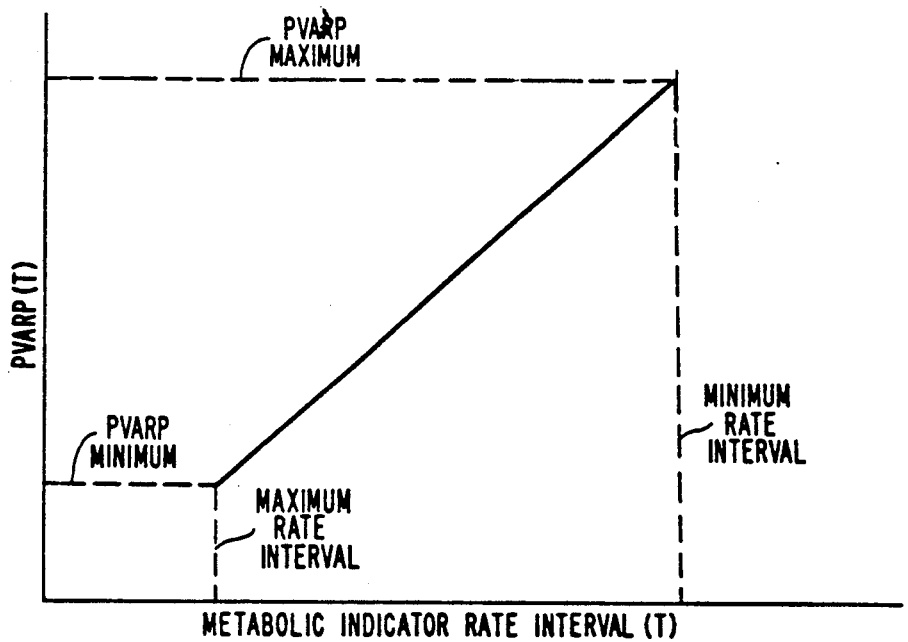
FIGS. 4A and 4B set forth graphic representations of the mechanism for automatically determining a rate adaptable PVARP interval from the metabolic indicator rate, in terms of cardiac cycle time and rate, respectively.
Figure 4B:
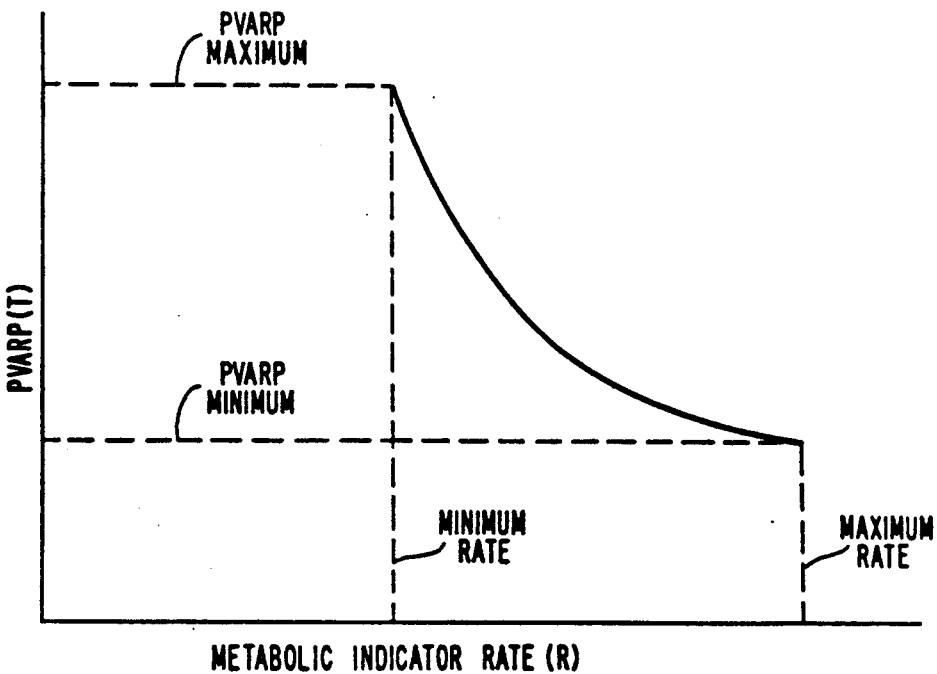

After pacing or sensing in the atrium, the pacemaker sets the A-V delay timer. The A-V delay interval ends with either ventricular sensing or time-out of the A-V delay timer. At the end of the A-V delay, the pacemaker is operating in the postventricular atrial refractory period (PVARP), the duration of which is based on the MIR parameter. The total atrial refactory period (TARP) is the interval corresponding to the maximum atrial tracking rate. The pacemaker divides the total atrail refractory period into two subintervals, the A-V delay interval and the PVARP interval, both of which are based on the reciprocal of the MIR. In this manner the pacemaker increases maximum atrial tracking rate with exercise by decreasing the PVARP as well as the A-V delay. FIGS. 4A and 4B illustrate The manner of determining the PVARP from the metabolic indicator rate or metabolic indicator rate interval. In the illustrative embodiment of the invention, the PVARP for the current metabolic indicator rate or rate interval is determined by linearly interpolating between two interval points. One point in FIG. 4A is defined by predetermined values of minimum rate interval and PVARP maximum, the other by maximum rate interval and PVARP minimum. FIG. 4B illustrates the PVARP determination method in terms of metabolic indicator rate. (One or both end points, for both the A-V delay and the PVARP curves, may be programmable parameters, as will be understood by those skilled in the art.)

Referring to FIGS. 5A and 5B, following every ventricular beat there is a PVARP interval during which the pacemaker should not sense P waves. If the pacer generates a ventricular stimulus for a given pacing cycle, it blanks the atrial sense amplifier immediately after the pace to ignore atrial signals which are unreliable in the aftermath of a ventricular stimulus. Blanking normally lasts for about 80 ms. For the duration of the PVARP (after the blanking period), the pacer enables atrial sensing. If the pacer senses a P wave during the PVARP, the atrial are beating too quickly. Because the PVARP is the interval immediately following the preceding A-V delay interval, any P wave occurring during the PVARP is too close to the preceding atrial beat. P waves falling during the PVARP control a switch from the DDDR mode to the VVIR mode. By using the metabolic indicator rate to decrease the PVARP during exercise, the atrial beats occurring more rapidly as the sinus rhythm increases are now less likely to fall in the PVARP. Consequently, by having the metabolic indicator rate control the PVARP, the metabolic indicator rate is able to extend the DDDR mode of operation during periods of even heavy exercise.

The final interval in the pacing cycle shown in FIGS. 5A and 5B is the atrial alert period. The end of the atrial alert period, measured from the end of the last atrial cardiac cycle, corresponds to the minimum cardiac pacing rate which, in the illustrative embodiment of the invention, is the current value of the metabolic indicator rate. A P wave falling after the PVARP but before the end of the atrial alert period has a rate lower than the maximum atrial tracking rate. Its rate is low enough to be considered nonpathological, so the pacemaker responds by triggering ventricular pacing in A-V synchrony (DDDR pacing). On the other hand, the pacer generates a stimulating pulse in the atrium if it does not detect natural atrial activity before the end of the alert period; the A-V timing is also triggered in this case as well.

FIGS. 3A through 4B illustrate how the total atrial refractory period (TARP) is determined. It consists of two components, the A-V delay and the PVARP, both of which may vary with the MIR. The minimum cardiac pacing rate equals the MIR, in the illustrative embodiment of the invention. The TARP is a programmable precentage (for example about 75 percent) of the overall cycle length (the reciprocal of the MIR). The exact percentage varies depending on the functions which set the A-V delay and the PVARP.

Figure 6:
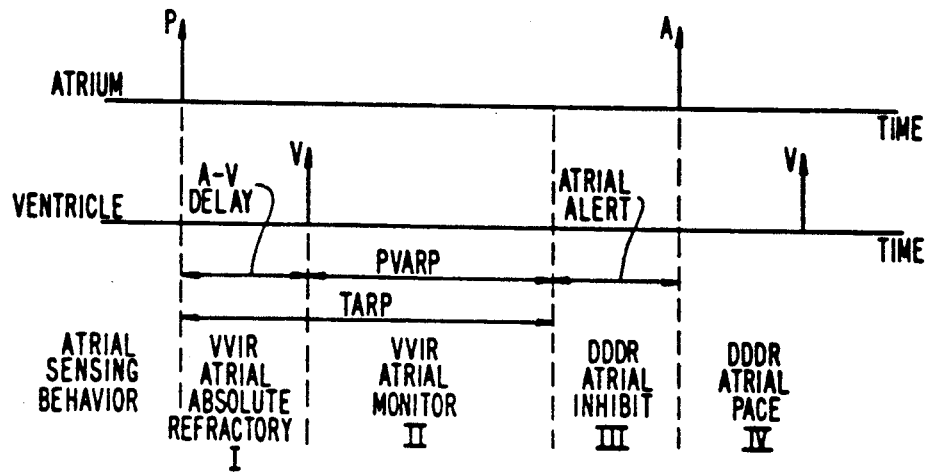
FIG. 6 is a timing diagram of a cardiac cycle and its associated time intervals indicating how the pacemaker responds to a cardiac event when sensed in different timed intervals.
Figure 7A:
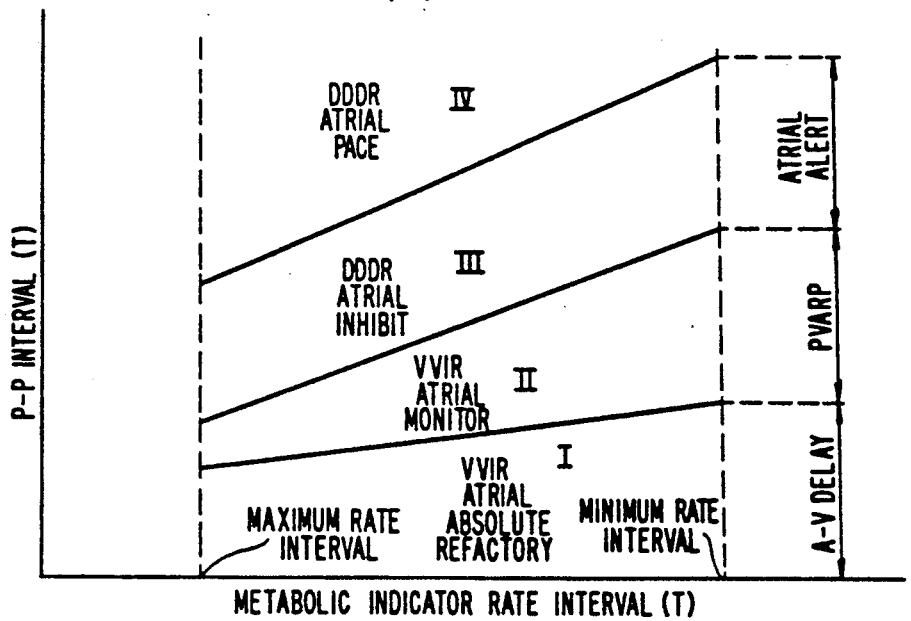
FIGS. 7A and 7B are graphs relating the rate of natural atrial sensing to the metabolic indicator rate parameter, in terms of cardiac cycle time and rate, respectively (the pacemaker bases the time boundaries for all intervals shown in FIGS. 3A to 4B on the metabolic indicator rate, while FIGS. 7A and 7B indicate how the pacemaker responds to a natural atrial depolarization as a function of metabolic indicator rate)
Figure 7B:
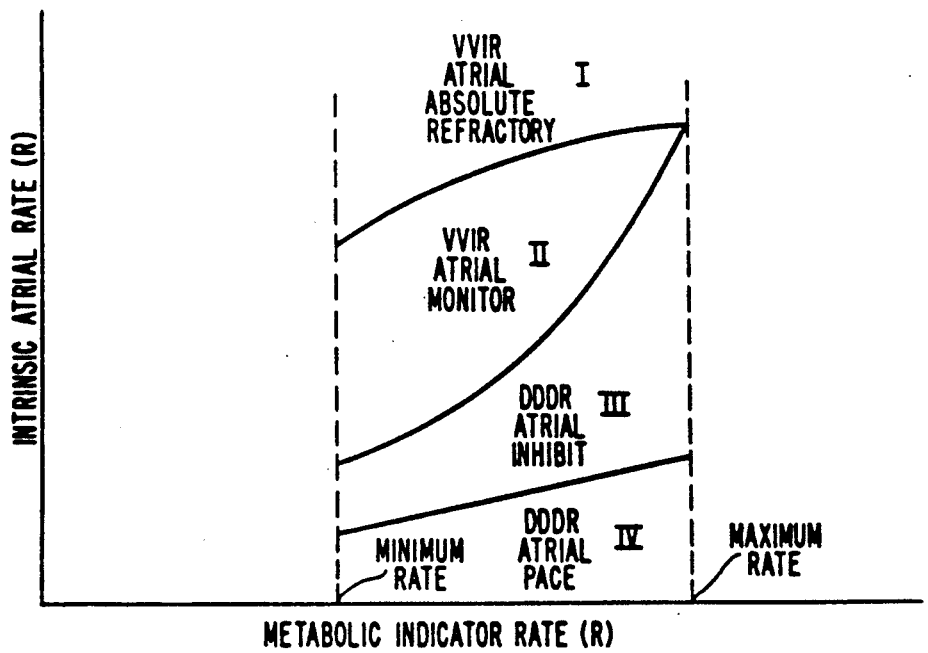

The timing diagram in FIG. 6 and the graphs of FIGS. 7A and 7B illustrate the manner of operation of the invention (FIG. 7B is derived from FIG. 7A simply by converting time values to the corresponding rates). When the metabolic indicator rate sets the maximum atrial tracking rate above the intrinsic atrial rate, sensed P waves will fall in the atrial alert interval and the effective pacing rate is under control of the sinus node. Operating in this manner, an atrial beat triggers the A-V delay, as in standard DDD pacing, but with the metabolic indicator rate automatically and continuously determining both the duration of the A-V delay and the cardiac cycle length. Pacing under these circumstances may be called the DDDR atrial inhibit mode because pacing is A-V synchronous with sensing inhibiting pacing in the ventricle and with the overall pacing rate determined by a metabolic (rate-responsive) sensor. This type of operation is represented by region III in FIGS. 6, 7A and 7B.

The metabolic indicator rate takes control only when the intrinsic atrial rate is too low or too high. If the intrinsic atrial rate is too low, causing time-out of the atrial alert timer as shown in FIG. 6, the pacemaker stimulates the atrium at the metabolic indicator rate and stimulates the ventricle after the A-V delay interval, unless natural ventricular activity inhibits pacing, region IV in FIGS. 6, 7A and 7B.

If the intrinsic atrial rate is faster than the maximum atrial tracking rate, the sinus rate is too high and the pacer senses during the PVARP as shown in region II of FIG. 6. Here, the pacer responds by ignoring atrial sensing for purposes of triggering ventricular stimulation and begins operation in the VVIR mode, standard pacemaker VVI but with the rate set to the metabolic indicator rate. (If the pacer senses a P wave in region I, during the A-V delay, it ignores it for all purposes.) The pacemaker switches operation from the DDDR to the VVIR mode when the intrinsic atrial rate is faster than the maximum atrial tracking rate. In the illustrative embodiment of the invention, the pacemaker switches to the VVIR mode when P waves fall within the PVARP interval for a predetermined number of consecutive cardiac cycles.

The mechanism for switching back to the DDDR pacing mode upon atrial rate slowing is the atrial activity monitor. In the VVIR mode, the pacer continues to detect atrial sensing to determine whether the intrinsic atrial rate remains faster than the maximum atrial tracking rate. While operating the VVIR mode, as in the DDDR mode, the pacer measures the metabolic indicator rate and accordingly updates the TARP. The pacer senses P waves and determines whether the P-P interval is longer than or shorter than the TARP. The pacer only senses these P waves to determine whether it can switch back to the DDDR mode. The atrial monitor is a counter which the pacer increments to a maximum of three when a P-P interval is shorter than the TARP and decrements to a minimum of zero when a P-P interval is longer than the TARP. The pacer initiates the VVIR mode when operating in the DDDR mode upon sensing a preset number of consecutive cardiac cycles in which P waves occur with the PVARP. The pacemaker increments the atrial activity monitor counter from zero to one upon the first sensed P wave during PVARP and increments the monitor for each succeeding P wave sensed during PVARP. If the pacer senses P waves in PVARP for the preset number of consecutive cardiac cycles it switches to VVIR pacing mode and then operates in the VVIR mode as long as the count is greater than zero. For example, if two cardiac cycles with premature P waves are required to cause the pacer to function in VVIR mode and two consecutive premature P waves are followed by two P waves separated by intervals longer than the TARP, the pacer decrements the atrial activity monitor counter back to zero and returns to operating in the DDDR mode in the following cardiac cycle. However, if several P waves occur at intervals shorter than the TARP, or more accurately if more P-P intervals are shorter than the TARP than are longer, the pacer increments the atrial activity monitor counter up to a maximum of three. This requires a sequence during which there are three more P-P intervals longer than the TARP than P-P intervals shorter than the TARP before the pacer decrements the counter back to zero and switches back to the DDDR mode. In this manner, the pacer distinguishes between isolated premature atrial depolarizations and atrial tachycardia. For an isolated premature atrial depolarization the pacemaker continues to operate in DDDR mode without interruption. Infrequent consecutive premature P waves cause the ventricle to perform asynchronously with respect to the atrium for only a few cycles. In the case of atrial tachycardia, the pacemaker will maintain VVIR pacing, requiring greater assurance of termination of the tachycardia episode before switching back to DDDR operation.

Figure 8:
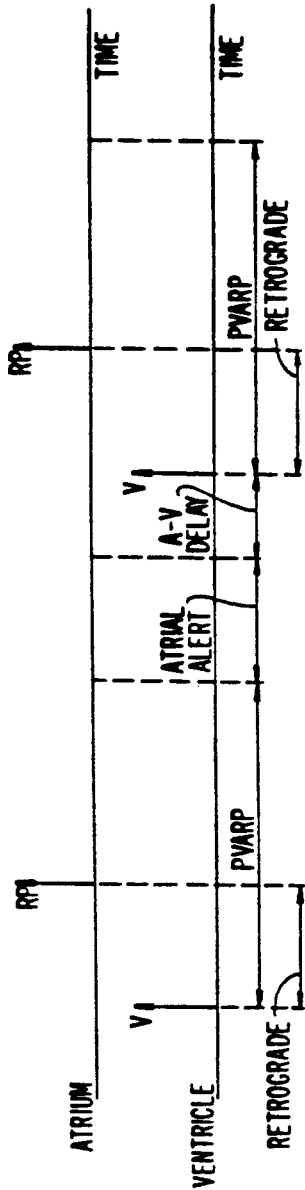
FIG. 8 is a timing diagram illustrating pacemaker operation in the presence of retrograde conduction leading to pacemaker-mediated VVIR mode (after the pacer generates a ventricular pacing pulse, retrograde conduction causes sensing of a P wave in the atrium within the PVARP, identified by the RP notation, even though the P-P interval is larger than the interval corresponding to the maximum atrial tracking rate)

When the pacer responds to an elevated atrial rate by pacing in the VVIR mode, A-V synchrony no longer exists. By generating stimulating pulses in the ventricle when a patient has intact retrograde (V-A) conduction pathways, depolarizations in the atrium may be caused by retrograde ventricular stimulation. These retrograde depolarizations can cause atrial P wave sensing to continually fall within the PVARP interval, locking the pacer into the VVIR mode, even though the actual P-P interval does not indicate the presence of tachycardia. FIG. 8 illustrates the phenomenon of pacemaker-mediated VVIR operation (PMVVIR), with the symbol RP representing a retrograde P wave. When operating in the DDDR mode, atrial sensing within the PVARP signifies an intrinsic atrial rate faster than the maximum atrial tracking rate. In the VVIR mode, the ventricle is not performing in synchrony with the atrium, and the atrial and ventricular cardiac cycles are independent. Atrial sensing during the PVARP does not necessarily indicate a high atrial rate; it only shows that atrial sensing is premature with respect to the ventricle. To determine whether the atrial beats are too fast, the pacemaker measures the P-P interval independent of the PVARP. If the P-P interval is not too short and atrial sensing occurs in the PVARP, PMVVIR exists.

The pacemaker uses a mechanism, the retrograde monitor, to detect and terminate the PMVVIR condition. When the pacer senses an atrial depolarization event during the PVARP while operating in the VVIR mode, it is either a tachycardia rate P wave or a retrograde depolarization. The pacemaker measures the time between this and the previous atrial sensed event. If the P-P interval is longer than the reciprocal of the maximum atrial tracking rate, the depolarization may be a retrograde P wave. The pacer is not certain that the atrial depolarization is retrograde because of the possibility of a P wave not being sensed. For the first 80 ms of the PVARP after generating a pacing stimulus, the pacer blank atrial sensing which the ventricular stimulus masks. Since an intrinsic atrial depolarization may occur during this blanking, a P wave may not have been sensed. Due to this uncertainty, the pacemaker uses a measure to better determine whether P waves arise from retrograde conduction. The retrograde monitor performs the analysis.

The retrograde monitor counts consecutive cycles having the PMVVIR characteristic, atrial sensing in the PVARP and a non-tachycardia atrial rate. The number of consecutive PMVVIR cycles which trigger the terminating mechanism is set to a value in the range from three to eight (typically five) to best prevent false PMVVIR operation.

Figure 9A:
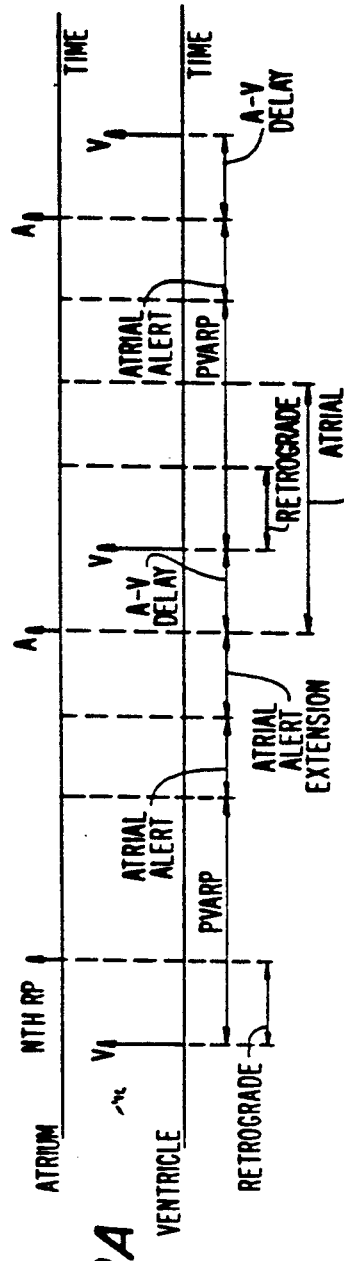
FIGS. 9A and 9B are timing diagrams illustrating how the pacemaker responds to terminate PMVVIR by extending the timer for the atrial alert period sufficiently to allow the atrium to repolarize following the retrograde depolarization.
Figure 9B:
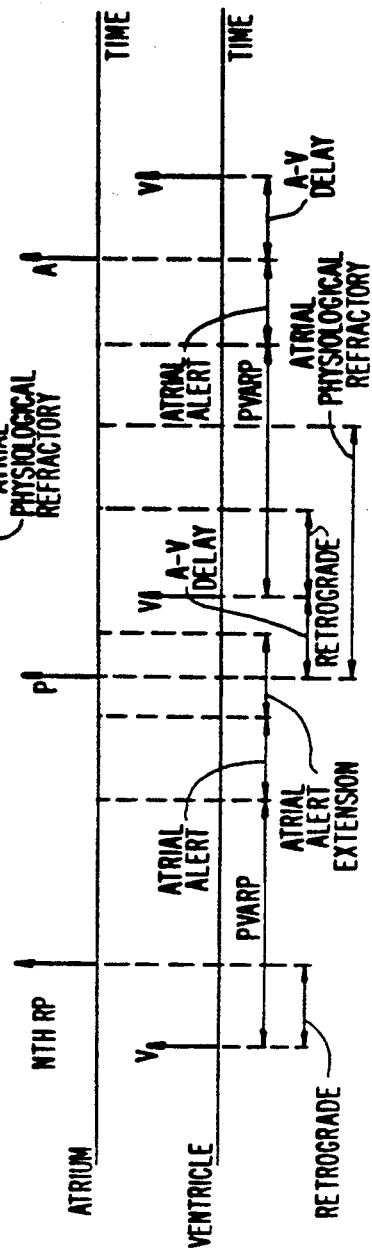

When the pacemaker detects PMVVIR, it terminates the condition using a pacing cycle extension mechanism illustrated by FIGS. 9A and 9B. When the pacer detects the preset number of consecutive refractory P waves (nth RP), it ignores subsequent P waves falling in the current PVARP interval and extends the atrial cycle timer by a time interval (200 to 300 ms of Atrial Alert Extension) sufficient to allow the atrium to recover from the retrograde depolarization so that the next atrial stimulus re-establishes A-V synchrony. The object is to allow subsequent retrograde conduction from the ventricle to occur when the atrium cannot depolarize in response to the retrograde depolarization, during the atrial physiological refractory period. FIG. 9A illustrates the generation of an atrial stimulus following the atrial alert extension. The ventricular beat after the A-V delay and the retrograde depolarization now occur during the atrial physiological refractory interval of the heart. Consequently, the retrograde phenomenon does not trigger another atrial beat. FIG. 9B shows the same thing but in this case a P wave (not a retrograde P wave) is sensed during the atrial alert extension. Once again, however, the retrograde depolarization takes place while the atrial are physiologically refractory.

Figure 10:
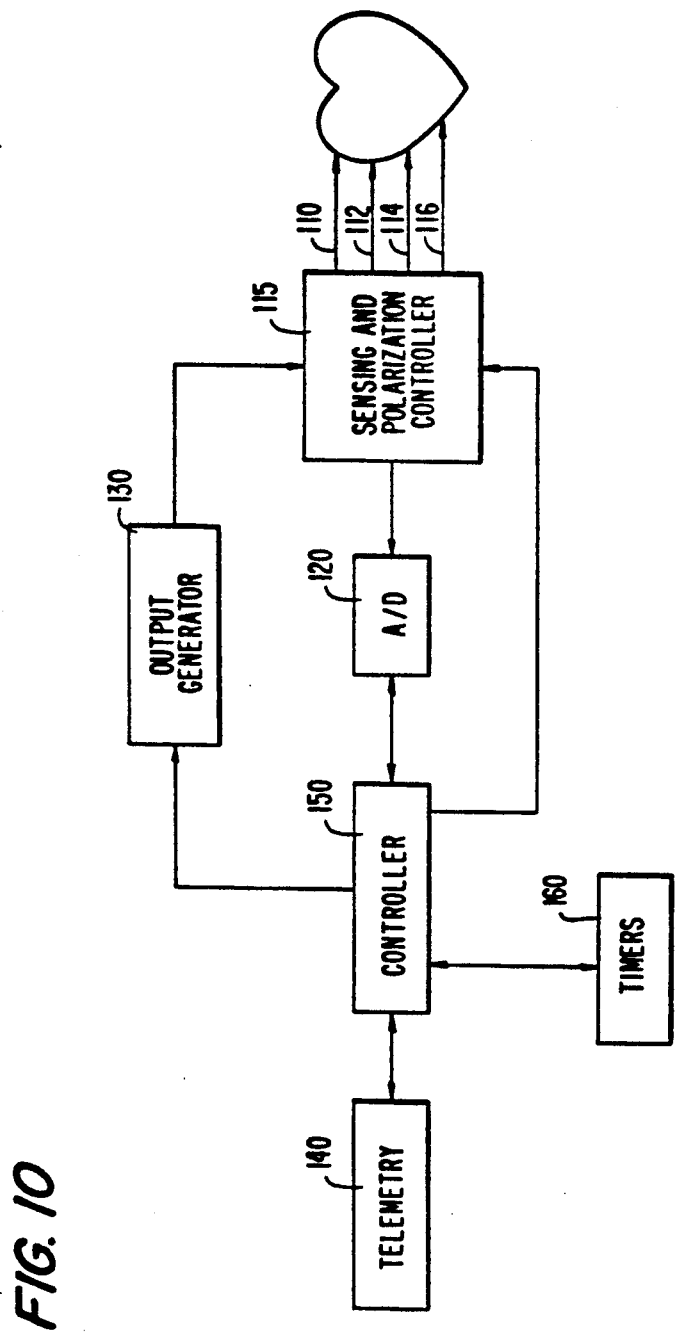
FIG. 10 is a high-level block diagram of the illustrative embodiment of our invention.

The drawing of FIG. 10 is a high-level block schematic illustrating one embodiment of pacemaker circuitry supporting the functions and methods comprising the illustrative embodiment of the invention. Other circuits which are common in cardiac pacemakers may be used to perform similar timing, sensing, and pulse generation functions. Tip and ring electrodes 110, 112, 114, 116 are those found in a conventional bipolar lead. All pacemaker logic is under control of controller 150 (which may include a microprocessor). The controller operates various switches to control: (1) enabling or disabling of sensing of intrinsic cardiac activity in the atrium (ASENSE) and the (VSENSE) by means of control signals to the Sensing and Polarization controller 115; (2) pace generation in the atrium (APACE) and the ventricle (VPACE) by sending control signals to the output generator block 130; (3) timers 160; (4) electrocardiogram sensing in the atrium (AECG) and ventricle (VECG) using A/D converter 120; and (5) telemetry block 140. In particular, the controller times activation and inhibition of stimulating pulse delivery, controls the amplitude and form of each pulse, controls sensing of natural cardiac signals ASENSE and VSENSE, and acquires sensed AECG and VECG waveforms.

Timers 160 are all down counters which time intervals determined by the controller. A timer counts to zero and, upon reaching a count of zero, notifies the controller of the expired interval by means of a time-out.

Figure 11:
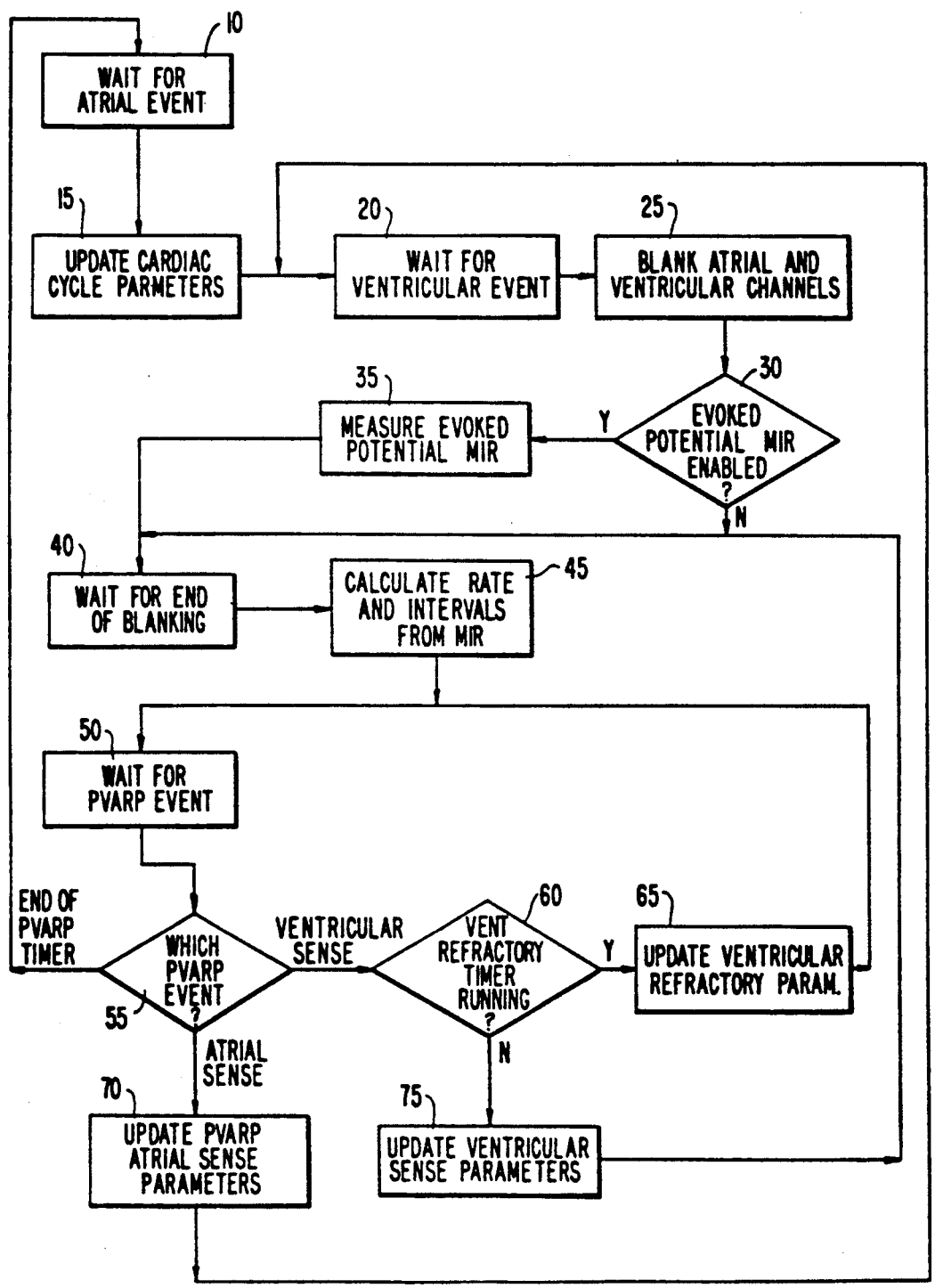
FIG. 11 is a flow diagram illustrating timing, cardiac polarization event detection, and operations performed in the illustrative embodiment of the invention.

FIG. 11 is the flow diagram showing control operations performed by the pacemaker as time proceeds within a single cardiac cycle. The pacemaker continuously repeats the cycle. The first block 10 represents the atrial alert wait state. Here the pacemaker waits for either ASENSE or the time-out of the atrial timer (one of Timers 160 of FIG. 10), defining the end of one cardiac cycle and the beginning of the next. Provided the pacemaker is functioning in DDDR mode, as controlled by the atrial activity monitor (AAM) and a counter of consecutive P waves sensed during PVARP (both operations are described in detail in the discussion of block 45), the pacer generates an atrial stimulus on time-out of the atrial timer. It is this block that the pacemaker controls VVIR or DDDR operation by determining whether to generate an atrial stimulus.

Our illustrative pacemaker uses atrial event timing as a basic for timing other events in the cardiac cycle. Atrial-based timing allows implementation of the automatic A-V delay feature of this invention more easliy than an implementation which maintains rate according to ventricular-based timing (although the latter is not excluded). Most other dual-chamber pacemaker use a constant ventricular-to-atrial (V-A) interval approach. The pacemaker of this invention sets the cardiac rate according to the atrial-to-atrial (A-A) interval. The pacer reverts to a rate defined by the V-A interval only after a premature ventricular contraction (PVC-ventricular R wave sensing before pacing or sensing in the atrium within the cardiac cycle) where maintaining the A-A interval timing would cause an excessively fast ventricular pacing rate. Otherwise, the pacer adjusts the A-V delay and the V-A interval follows accordingly to maintain a P wave to atrial pacing (P-A) or A-A interval correlated with the metabolic indicator rate, regardless of variations in atrial-to-ventricular event timing.

Following the atrial event (sense or pace), the pacemaker updates cardiac cycle control parameters, enables timers and sensing where appropriate in the atrium and ventricle, and processes the atrial activity monitor (AAM) and the retrograde monitor in update cardiac cycle parameters block 15. How the pacemaker controls cardiac cycle parameters depends on whether the event ending the cardiac cycle was ASENSE or atrial timer time-out and for either of these events, whether the pacemaker is operating in an A-V synchronous dual-chamber manner or temporarily in the VVIR mode in response to atrial tachycardia or retrograde conduction. In this step, the pacer performs timing, sensing, data logging, atrial activity monitor, and retrograde monitor operations.

The pacer first updates the cardiac cycle interval data log by setting the current P wave to P wave (P-P) interval log to: (1) the time loaded into the atrial timer at the time of the atrial event in the previous cardiac cycle if the current atrial event is atrial timer time-out, or (2) in the case of ASENSE, the time in (1) reduced by the time remaining in the atrial timer.

The pacer now services the atrial activity monitor (AAM). The AAM monitors the timing and recent history of cardiac cycles depending on whether the intrinsic atrial rate for a cycle is faster or slower than the maximum atrial tracking rate. If the pacer is operating temporarily in the VVIR mode in response to an atrial rate faster than the maximum atrial tracking rate and the atrial rate begins to slow below that rate, the AAM acts in a controlled manner to delay the enabling of atrial pacing and sensing and synchronizing the heart chambers to pace in the DDDR mode. The amount of delay depends on the how long the high atrial rate has prevailed. AAM informational parameters may include combinations of one or more of: high atrial rate counters, low atrial rate counters, and history buffers expressing which of the last cardiac cycles had high and low rates. Linear and nonlinear control methods may use the informational parameters to time the recovery from high atrial rates. The illustrative embodiment of the invention uses a single counter, the AAM counter, which the pacer increments for atrial tachycardia rates and decrements for slower atrial rates. At this point in the control flow, the pacer decrements the AAM counter by one (unless it is already at the minimum of zero). The reason for this is that the branch to block 10, which precedes block 15, is from block 55 in which the pacer determines that the P-P interval is longer than the TARP. If the AAM counter reaches a minimum of zero, the pacer will change modes from temporary VVIR to DDDR, but this will occur in an operation later in the cardiac cycle. The pacer increments or decrements the AAM counter for every sensed P wave and atrial pace delivery regardless of the pacer's current operating mode.

The pacemaker begins timing the next A-A interval by intializing the atrial timer to the interval specified by the metabolic indicator rate (MIR). This interval, in milliseconds, is 60,000 divided by the MIR (in beats per minute). Generally, the pacemaker sets the A-A interval timer to the interval set by the MIR. However, in circumstances in which the pacemaker is changing operation between the VVIR and the DDDR modes, it may be appropriate for the pacer to set an A-A interval value different from that consistent with the MIR. For example, when switching from the DDDR mode where the rate has been driven by a high intrinsic atrial rate to a VVIR mode at the MIR, gradually ramping down the rate from the intrinsic atrial rate to the MIR is a possibility. Likewise, when changing from the VVIR to the DDDR mode, the pacer may gradually reduces the A-A interval from that set from the MIR to one consistent with the sensed intrinsic atrial rate.

If the pacer is operating in the DDDR mode, it generates a stimulating pulse (APACE). Also after atrial timer time-out, the pacer divides the A-V delay interval into two subintervals timed by a subinterval timer. In the first blanking interval typically 80 milliseconds, the pacer disables ASENSE and VSENSE for long enough to prevent sensing of the atrial pacing pulse, it artifact, and any evoked potential. After the subinterval timer time-out, the pacer resets the subinterval timer to an interval which, when added to the first blanking interval, sets the automatic A-V delay interval. The pacer enables VSENSE at this time to allow intrinsic ventricular R waves to inhibit VPACE.

If the event ending the cardiac cycle was ASENSE and the pacer is operating in the DDDR mode, it sets the A-V delay interval timer offset by a latency factor. The A-V delay value is based on the time between APACE and VSENSE for normal atrioventricular conduction for the patient. The pacer modifies the A-V delay by a latency factor, as is known in the art, to account for differences in conduction time between paced atrial activity (APACE) and intrinsic atrial activity (ASENSE). The value of the latency factor may vary depending on such conditions as location of the leads, atrial sense threshold, and atrial sensitivity. At the subsequent A-V delay time-out, the pacer will stimulate the ventricle (VPACE), unless pacing is inhibited by VSENSE. During the A-V delay interval, the pacer disables ASENSE.

The retrograde monitor operates by counting consecutive cardiac cycles in which sensed atrial events occur during the PVARP interval while a running average (over about four cycles) of the P-P interval log corresponds to a rate slower than the maximum atrial tracking rate. An ASENSE occurring subsequent to the PVARP interval or an atrial cycle time-out breaks any string of consecutive retrograde cycles. At this point in the control flow, the pacer resets the retrograde monitor to zero because the consecutive count has been broken.

Block 20 represents the ventricular alert wait state. Here the pacemaker waits for either VSENSE or the time-out of the A-V delay interval, Upon either event, in the blanking control operation of block 25, the pacer disables ASENSE and VSENSE and times a blanking interval corresponding to the atrial absolute refractory period (AARP). Within the AARP, natural P waves cannot physiologically occur, so the pacer blanks to avoid atrial sensing of such extraneous events as ventricular stimulation, stimulus artifact, and evoked potential. If the ventricular event was time-out of the A-V delay timer rather than VSENSE, then the pacer generates a stimulating pulse (VPACE).

If the pacemaker metabolic indicator system uses evoked potential sensing, determined in block 30, the pacemaker performs the evoked potential MIR measurement and rate determination in block 35. (The illustrative embodiment of the invention includes a mechanism for enabling or disabling each MIR system using telemetry).

The pacer waits for the end of blanking in block 40. It is in block 45 that the MIR is used to calculate the new A-V delay and PVARP values as well as the new cycle length (A-A interval). Also, PVARP timing begins. Since the pacer traverses this flow path during every cardiac cycle, in the illustrative embodiment of the invention important rate and interval control operations are performed during the rate and interval calculating block 45.

The next operation performed in the rate and interval calculating block 45 of FIG. 11 is determination of the maximum atrial tracking rate from the A-V delay and the PVARP. The maximum atrial tracking rate is the inverse of the total atrial refractory period where the TARP is the sum of the A-V delay and the PVARP. Because the pacer automatically determines both the A-V delay and the PVARP as functions of metabolic indicator rate, maximum atrial tracking rate is likewise a function of MIR. The maximum atrial tracking rate defines the boundary between DDDR and VVIR-type pacing in the illustrative embodiment of the invention.

If the pacemaker must sense P waves during PVARP for two consecutive cardiac cycles while functioning in DDDR mode to trigger the change to VVIR mode, the pacer will sustain A-V synchronous pacing in response to a single premature atrial contraction. If the pacer begins pacing temporarily in the VVIR mode because of two premature atrial contractions, the AAM counter only has to decrement in block 15 from two to zero before restoring DDDR mode operations in the following cardiac cycle. If the pacer performs in the VVIR mode due to atrial tachycardia, the AAM counter will increment (in block 70, to be described below) to the maximum value of three. The AAM counter must decrement for at least three cycles after the tachycardia terminates before the pacer can restore atrial pacing. But there is an additional mechanism for resetting the AAM counter to zero in order to rapidly restore atrial pacing. In block 45, a two-second timer determines whether atrial sensing has not taken place for two seconds. In the absence of atrial sensing. there is not tachycardia and therefore, no need to inhibit atrial pacing. Consequently the pacer resets the AAM counter to zero.

In the final operation within the rate and interval calculation block 45, the pacer prepares for atrial and ventricular refractory operations. In the atrium, the pacer enables ASENSE for sensing during the newly determined PVARP interval. The pacer delays ventricular sensing until the end of the ventricular blanking period (70 milliseconds beyond the 80-ms atrial blanking period) because VSENSE during the ventricular absolute refractory period is not a significant event with regard to cardiac physiology (any sensed signal must be noise).

The pacer now waits for ASENSE, VSENSE, and PVARP timer events during the wait for PVARP event block 50. Logic blocks 55 and 60 determine control flow upon one of the three events. Time-out of the PVARP timer ends the PVARP, after which block 55 controls a branch to wait for atrial event block 10; the atrial alert period always follows a PVARP time-out.

If the PVARP event is a ventricular sense, then in block 60 the pacer makes a test to determine whetehr a ventricular refractory timer is running. As described above, initially the pacer times a 70 millisecond absolute refractory interval. The pacemaker ignores all ventricular sense events which occur during this interval. After this absolute refractory interval, the pacer times a 150 millisecond relative refractory interval. An R wave sensed during the relative refractory interval restarts the 150-ms timer but otherwise has no effect (the R wave is treated as noise and is ignored). The pacer's control flow enters block 65 within the first 70 milliseconds of the ventricular refractory timer, the pacer ignores the ventricular sense event and returns to block 50 where the system again waits for a PVARP event. If the pacer enters block 65 before time-out of the ventricular refractory timer (i.e., within 220 milliseconds after the beginning of the PVARP interval), the pace restarts the timer and the system notes that relative refractory timing is in progress. Subsequent entries into block 65 do the same thing; in every case the pacer returns control to block 50. If a ventricular sense event occurs when the timer has proceeded beyond 150 milliseconds in a relative refractory interval, it is an indication that a premature ventricular contraction has occurred, i.e., a ventricular beat during the PVARP but after the ventricular absolute and relative refractory periods.

The pacer responds to a premature ventricular contraction sensing in update ventricular sense parameters block 75 and then branches to the wait for end of blanking block 40. Atrial events should always precede ventricular events. Occurrence of a premature ventricular event, one anticipating the atrial event for that cardiac cycle, signifies the end of the cardiac cycle. The pacer moves on to the next cardiac cycle by disabling ASENSE and VSENSE in block 75 and then branching to block 40 since a ventricular event has just occurred. But there is one modification to the usual processing which is required. There is a timer running which times the A-A interval. This timer requires a new value. Instead of timing a full cycle from the last P wave or APACE, what is required is timing of the V-A interval from the R wave just sensed. The pacer subtracts the A-V delay from the total A-A cycle length (the time loaded into the A-A timer in block 15), and uses the resulting V-A interval to set the timer defining the time-out event ending block 10.

In the update PVARP atrial sense parameters block 70, the pacemaker services ASENSE events falling within the PVARP interval. First the pacer measures the immediate P wave to P wave (P-P) interval by reducing the timer interval last loaded into the atrial timer by the time left in the atrial timer. The current instantaneous atrial timer value holds the time left in the atrial cycle because the timer, like all timers, is a down counter. The pacer uses the latest P-P interval value to update the running P-P interval average which is required for retrograde monitor processing. The pacer services the atrial activity monitor (AAM) by incrementing the AAM counter to a maximum of three since, in this instance, the P-P interval is shorter than the TARP. Also, the pacer sets the A-A interval timer, the A-V delay, and the blanking interval just as they are set in block 15.

The pacemaker now processes the retrograde monitor in updage PVARP atrial sense parameters block 70. The action of temporarily changing the operating mode from DDDR to VVIR creates the problem of a new form of PMT, Pacer-Mediated VVIR (PMVVIR). This phenomenon occurs when retrograde conduction during the VVIR mode causes a P wave to consistently fall in the PVARP.

The retrograde monitor detects and terminates retrograde (V-A) conduction. The first step toward detecting PMVVIR is defining it within the scope of the invention. The characterization of PMVVIR within a cardiac cycle is: (a) a P wave occurring within the PVARP, when (b) the P-P interval running average is larger than the maximum atrial tracking rate interval. The retrograde monitor in update PVARP atrial sense parameters block 70 detects PMVVIR by counting such events while the pacer is functioning in VVIR mode in response to pathological atrial tachycardias. If a predefined number (five in the preferred embodiment of the invention) of consecutive retrograde cycles occur, the retrograde monitor classifies the phenomenon as PMVVIR and begins its reversion response.

The retrograde monitor terminates the PMVVIR retrograde conduction condition using a pacing cycle extension mechanism wherein the pacer extends one cardiac cycle (A-A interval, timed by the atrial timer) by a predetermined amount (for example, 240 ms). This terminates the PMVVIR condition by restoring A-V synchrony. The pacemaker makes a branch to block 20 to wait for a ventricular event; the actual A-A cycle extension occurs in the next loop where. block 10 is extended. To insure that the pacer reaches block 10 requires a branch during the next cycle from block 55 to block 10. To guarantee this branch, part of the retrograde monitor processing in block 70 includes setting a flag which causes both atrial and ventricular sense events to be ignored during the next cycle in block 55. The retrograde monitor processing also includes the step of setting the AAM counter to zero so that the DDDR mode of operation can resume upon the next entry into block 10.

Although the invention has been described with reference to a particular embodiment, it is to be understood that this embodiment is merely illustrative of the application of the principles of the invention. Numerous modifications may be made therein and other arrangements may be devised without departing from the spirit and the scope of the invention.

We claim:

1. A dual-chamber rate-responsive pacemaker, comprising:
   means for generating ventricular pacing pulses,
   means for sensing atrial heartbeats,
   means responsive to said atrial heartbeat sensing means for deriving an indication oof intrinsic atrial rate,
   sensor means for determining a metabolic indicator rate,
   means for determining a maximum atrial tracking rate as a function of said metabolic indicator rate,
   means for comparing said intrinsic atrial rate indication to said maximum atrial tracking rate, and
   means responsive to said comparing means for controlling said generating means to operate in a first mode in which ventricular pacing pulses are generated in synchrony with operations of said atrial heartbeat sensing means when said intrinsic atrial rate indication is slower than said maximum atrial tracking rate, and for controlling said generating means to operate in a second mode in which ventricular pacing pulses are generated at a rate which is a function of said metabolic indicator rate, with timing independent of said atrial heartbeat sensing means, when said intrinsic atrial rate indication exceeds said maximum atrial tracking rate,
   said controlling means including:
   means responsive to said comparing means for developing a record of the occurrence of recent cardiac cycles in hich said intrinsic rate exceeded said maximum atrial tracking rate,
   decision means for deciding whether said record meets a predetermined criterion, and
   means responsive to said decision means for governing whether said ventricular pacing pulse generating means operates in said first or said second mode.

2. A dual-chamber rate-responsive pacemaker in accordance with claim 1 wherein said decision means decides on a change from said first mode to said second mode when the intrinsic atrial exceeds the maximum atrial tracking rate in a predetermined percentage of the most recent cardiac cycles, and decides on a change from said second mode to said first mode when the intrinsic atrial rate was slower than said maximum atrial tracking rate in a second predetermined percentage of the most recent cardiac cycles.

3. A dual-chamber rate-responsive pacemaker, comprising:
   means for generating ventricular pacing pulses,
   means for sensing atrial heartbeats,
   means responsive to said atrial heartbeat sensing means for deriving an indication of intrinsic atrial rate,
   sensor means for determining a metabolic indicator rate,
   means for determining a maximum atrial tracking rate as a function of said metabolic indicator rate,
   means for comparing said intrinsic atrial rate indication to said maximum atrial tracking rate, and
   means responsive to said comparing means for controlling said generating mmeans to operate in a first mode in which ventricular pacing pulses are generated in synchrony with operations of said atrial heartbeat sensing means when said intrinsic atrial rate indication is slower than said maximum atrial tracking rate, and for controlling said generating means to operate in a second in which ventricular pacing pulses are generated at a rate which is a function of said metabolic indicator rate, with timing independent of said atrial heartbeat sensing means, when said intrinsic rate indication exceeds said maximum atrial tracking rate,
   said controlling mens including:
   means for timing a postventricular atrial refractory period following generation of a ventricular pacing pulse,
   means responsive to said comparing means for maintaining a record for recent cardiac cycles of which of said intrinsic atrial rate and said maximum atrial tracking rate was greater and whether said atrial heartbeat sensing means operated during a postventricular atrial refractory period,
   decision means for deciding whether said record meets a predetermined criterion, and
   means responsive to said decision means for governing whether said ventricular pacing pulse generating means operates in said first or said second mode.

4. A dual-chamber rate-responsive pacemaker in accordance with claim 3 wherein when said decision means decides on a switch from said second mode to said first mode, said controlling means temporarily increases the cycle time of the pacemaker.

5. A dual-chamber rate-responsive pacemaker in accordance with claim 1 or 2 wherein said ventricular pacing pulse generating means, when operating in synchrony with operations of said atrial heartbeat sensing means, generates a pulse after an A-V delay interval following an operation of said atrial heartbeat sensing means, and further including means for adjusting said A-V delay intervl to be a function of said metabolic indicator rate.

6. A dual-chamber rate-responsive pacemaker, comprising:
   means for generating ventricular pacing pulses,
   means for sensing atrial heartbeats,
   sensor means for deriving a metabolic indicator rate
   means for setting at least one atrial refractory period as a function of said metabolic indicator rate,
   means responsive to said atrial heartbeat sensing means for determining whether sensed atrial heartbeats fall within at least one of said atrial refractory periods, and
   means responsive to said determining means for controlling a first operting mode in which said generating means generates ventricular pacing pulses in synchrony with sensed atrial heartbeats and a second operating mode in which said generating means generates ventricular pacing pulses at a rate which is a function of said metabolic indicator rate with timing independent of sensed atrial heartbeats.

7. A dual-chamber rate-responsive pacemaker in accordance with claim 6 wherein said controlling means, when operating in said first mode, controls said ventricular pulse generating means to generate a pulse following a sensed atrail heartbeat after an A-V delay interval which is a function of said metabolic indicator rate.

8. A dual-chamber rate-responsive pacemaker in accordance with claim 6 wherein said controlling means further includes:
means for storing information relating to recent cardiac cycles in which sensed atrial heartbeats fell within said postventricular atrial refractory period but after an A-V delay interval and in which the interval between sensed atrial heartbeats is shorter than said total atrial refractory period, and wherein said controlling means is further responsive to said storing means.

9. A dual-chamber rate-responsive pacemaker in accordance with claim 6 wherein said controlling means causes a change from said first mode to said second mode upon a predetermined percentage of sensed atrial heartbeats falling within said postventricular atrial refractory period but after an A-V delay interval, and said controlling means causes a change from said second mode to said first mode when the interval between sensed atrial heartbeats is longer than said total atrial refractory period in a predetermined preponderance of the most recent cardiac cycles.

10. A dual-chamber rate-responsive pacemaker in accordance with claim 6 wherein said controlling means includes:
means for maintaining a record of recent cardiac cycles in which atrial heartbeats fall within said postventricular atrial refractory period but occur at a physiological rate, and means responsive to said record maintaining means satisfying predetermined criteria for governing switches between said first and second operating modes.

11. A dual-chamber rate-responsive pacemaker in accordance with claim 10 wherein when said governing means causes a switch from said second mode to said first mode, said controlling means temporarily increases the cycle time of the pacemaker.

12. A dual-chamber rate-responsive pacemaker, comprising:
means for generating ventricular pacing pulses;
means for sensing atrial heartbeats;
means for determining a metabolic indicator rate;
means for deriving a maximum atrial tracking rate as a function of said metabolic indicator rate;
means for comparing said maximum atrial tracking rate with the rate of operation of said atrial heartbeat sensing means over a plurality of cardiac cycles, and depending on the pattern of the results of the comparison for classifying whether the atrial heartbeat rate is physiological or pathological; and
control means operative when the atrail heartbeat rate is physiological for keying the operation of said ventricular pacing pulse generating means to the operation of said atrial heartbeat sensing means, and operative when the atrial heartbeat rate is pathological for keying the operation of said ventricular pacing pulse generating means to said metabolic indicator rate independent of the operation of said atrial heartbeat sensing means.

13. A dual-chamber rate-responsive pacemaker in accordance with claim 12 wherein said comparing and classifying means operates to increase the highest atrial heartbeat rate which is still classified as physiological as the metabolic indicator rate increases.

14. A dual-chamber rate-responsive pacemaker in accordance with claim 13 wherein, when the atrial heartbeat rate is physiological, said ventricular pacing pulse generating means operates at a time after operation of said atrail heartbeat sensing means which decreases as the metabolic indicator rate increases.

15. A dual-chamber rate-responsive pacemaker in accordance with claim 14 further including means for generating atrial pacing pulses and means for sensing ventricular heartbeats; and wherein said control means, when the atrial heartbeat rate is physiological, controls DDD pacer operation with the cycle time being a function of said metabolic indicator rate.

16. A dual-chamber rate-responsive pacemaker in accordance with claim 15, wherein said comparing and classifying means operates, on average, to classify the atrial heartbeat rate as pathological in fewer heartbeat cycles than are required to classify the atrial heartbeat rate as physiological.

17. A dual-chamber rate-responsive pacemaker in accordance with claim 16, wherein said comparing and classifying means delays classifying a physiological atrial heartbeat rate as physiological a length of time which is an increasing function of the length of time during which the previous atrial heartbeat rate was classified as pathological.

18. A dual-chamber rate-responsive pacemaker in accordance with claim 17 wherein said comparing and classifying means includes means for timing a postventricular atrial refractory period ("PVARP") and operates to classify the atrail heartbeat rate as pathological when a predetermined percentage of atrial heartbeats are sensed during the PVARP; and further including means for determining a total atrail refractory period ("TARP"), means for timing the intervals between successively sensed atrial heartbeats and operating to classify the atrail heartbeat rate as pathological when the intervals are shorter than the TARP, and means responsive to a non-pathological rate being determined with a predetermined regularity simultaneously with said comparing and classifying means classifying the atrial heartbeat rate as pathological for extending the duration of a pacer cycle.

19. A dual-chamber rate-responsive pacemaker in accordance with claim 13 further including means for generating atrail pacing pulses and means for sensing ventricular heartbeats; and wherein said control means, when the atrail heartbeat rate is physiological, controls DDD pacer operation with the cycle time being function of said metabolic indicator rate.

20. A dual-chamber rate-responsive pacemaker in accordance with claim 13 wherein said comparing and classifying means operates, on average, to classify the atrial heartbeat rate as pathological in fewer heartbeat cycles than are required to classify the atrial heartbeat rate as physiological.

21. A dual-chamber rate-responsive pacemaker in accordance with claim 13 wherein said comparing and classifying means delays classifying a physiological atrial heartbeat rate as physiological a length of time which is an increasing function of the length of time during which the previous atrial heartbeat rate was classified as pathological.

22. A dual-chamber rate-responsive pacemaker in accordance with claim 13 wherein said comparing and classifying means includes means for timing a postventricular atrial refractory period ("PVARP") and operates to classify the atrial heartbeat rate as pathological when a predetermined percentage of atrial heartbeats are sensed during the PVARP; and further including means for determining a total atrial refractory period ("TARP"), means for timing the intervals between sucessively sensed atrial heartbeats and operating to classify the atrial heartbeat rate as pathological when the intervals are shorter than the TARP, and means responsive to a non-pathological rate being deteermined with a predetermined regularity simultaneously with said comparing and classifying means classifying the atrial heartbeat rate as pathological for extending the duration of a pacer cycle.

23. A dual-chamber rate-responsive pacemaker in accordance with claim 12 wherein, when the atrail heartbeat rate is physiological, said ventricular pacing pulse generating means operates at a time after operation of said atrial heartbeat sensing means which decreases as the metabolic indicator rate increases.

24. A dual-chamber rate-responsive pacemaker in accordance with claim 23 further including means for generating atrial pacing pulses and means for sensing ventricular heartbeats; and wherein said control means, when the atrial heartbeat rate is physiological, controls DDD pacer operation with the cycle time being a function of said metabolic indicator rate.

25. A dual-chamber rate-responsive pacemaker in accordance with claim 12 further including means for generating atrial pacing pulses and means for sensing ventricular heartbeats; and wherein said control means, when the atrial heartbeat rate is physiological, controls DDD pacer operation with the cycle time being a function of said metabolic indicator rate.

26. A dual-chamber rate-responsive pacemaker in accordance with claim 12 wherein said comparing and classifying means operates, on average, to classify the atrial heartbeat rate as pathological in fewer heartbeat cycles than are required to classify the atrial heartbeat rate as physiological.

27. A dual-chamber rate-responsive pacemaker in accordance with claim 26 wherein said comparing and classifying means delays classifying a physiological atrial heartbeat rate as physiological length of time which is an increasing function of the length of time during which the previous atrial heartbeat rate was classified as pathological.

28. A dual-chamber rate-responsive pacemaker in accordance with claim 12 wherein said comparing and classifying means delays classifying a physiological atrial heartbeat rate as physiological a length of time which is an increasing function of the length of time during which the previous atrial heartbeat rate was classified as pathological.

29. A dual-chamber rate-responsive pacemaker in accordance with claim 12 wherein said comparing and classifying means includes means for timing a postventricular atrial refractory period ("PVARP") and operates to classify the atrial heartbeat rate as pathological when a predetermined percentage of atrial heartbeats are sensed during the PVARP; and further including means for determining a total atrial refractory period ("TARP"), means for timing the intervals between successively sensed atrial heartbeats and operating to classify the atrial heartbeat rate as pathological when the intervals are shorter than the TARP, and means responsive to a non-pathological rate being determined with a predetermined regularity simultaneously with said comparing and classifying means classifying the atrial heartbeat rate as pathological for extending the duration of a pacer cycle.

30. A dual-chamber rate-responsive pacemaker, comprising:
means for generating atrial and ventricular pacing pulses;
means for sensing atrial and ventricular heartbeats;
means for determining a metabolic indicator rate;
means for ascertaining wherther sensed atrial heartbeats are occurring at a rate which is pathological for the current metabolic indicator rate; and
means for controlling said generating and sensing means to operate normally in a DDDR mode but to switch to a VVIR mode when the rate of the atrial heartbeats is pathological, said controlling means operating to switch between modes based on the most recent cardiac cycles, with fewer cardiac cycles being necessary to effect a switch from DDDR to VVIR mode than from VVIR to DDDR mode.

31. A dual-chamber rate-responsive pacemaker, comprising:
means for generating atrial and ventricular pacing pulses;
means for sensing atrial and ventricular heartbeats;
means for determining a metabolic indicator rate;
means for ascertaining whether sensed atrial heartbeats are occurring at a rate which is pathological for the current metabolic indicator rate;
means for controlling said generating and sensing means to operate normally in a DDDR mode but to switch to a VVIR mode when the rate of the atrial heartbeat is pathological;
means for detecting a PMVVIR condition when the pacemaker is operating in the VVIR mode; and
means responsive to said detecting means for controlling a switch from VVIR mode to DDDR mode and for temporarily extending the V-A interval in the DDDR mode.

32. A dual-chamber rate-responsive pacemaker in accordance with claim 30 or 31 wherein said ascertaining means operates to change the highest atrial heartbeat rate which is considered to be non-pathological as an increasing function of the metabolic indicator rate.

33. A dual-chamber rate-responsive pacemaker in accordance with claim 30 or 31 wherein, in the DDDR mode of operation, said controlling means operates to change the A-V delay as a decreasing function of the metabolic indicator rate.

34. A method of operating a dual-chamber rate-responsive pacemaker, comprising the step of:
generating ventricular pacing pulses,
sensing atrial heartbeats,
deriving an indication of intrinsic atrial rate in response to the sensing of atrial heartbeats,
determining a metabolic indicator rate,
determining a maximum atrial tracking rate as a function of said metabolic indicator rate,
comparing said intrinsic atrial rate indication to said maximum atrial tracking rate, and,
in response to said comparing step, controlling ventricular pacing pulse generation in a first mode in which ventricular pacing pulses are generated in synchrony with atrial heartbeat sensing when said intrinsic atrail rate indication is slower than said maximum atrail tracking rate, and controlling ventricular pacing pulse generation in a second mode in which ventricular pacing pulses are generated at a rate which is a function of said metabolic inidator rate, with timing independent of atrial heartbeat sensing, when said intrinsic atrail rate indication exceeds said maximum atrial tracking rate.

said controlling step including the sub-steps of:

developing a record of the occurrence of recent cardiac cylces in which said intrinsic atrial rate exceeded said maximum atrial tracking rate, deciding whether said record meets a predetermined criterion, and governing whether ventricular pacing pulses are generated in said first or said second mode in accordance with whether said predetermined criterion is met.

35. A method of operating a dual-chamber rate-responsive pacemaker in accordance with claim 34 wherein a change is made from said first mode to said second mode when the intrinsic atrial rate exceeds the maximum atrial tracking rate in a predetermined percentage of the most recent cardiac cycles, and a change is made from said second mode to said first mode when the intrinsic atrial rate was slower than said maximum atrial tracking rate in a second predetermined percentage of the most recent cardiac cycles.

36. A method of operating a dual-chamber rate-responsive pacemaker, comprising the steps of:

generating ventricular pacing pulses, sensing atrial heartbeats, deriving an indication of intrinsic atrial rate in response to the sensing of atrial heartbeats, determining a metabolic indicator rate, determining a maximum atrial tracking rate as a function of said metabolic indicator rate, comparing said intrinsic atrial rate indication to said maximum atrial tracking rate, and in response to said comparing step, controlling ventricular pacing pulse generation in a first mode in which ventricular pacing pulses are generated in synchrony with atrial heartbeat sensing when said intrinsic atrial rate indication is slower than said maximum atrial tracking rate, and controlling ventricular pacing pulse generation in a second mode in which ventricular pacing pulses are generated at a rate which is a function of said metabolic indicator rate, with timing independent of atrial heartbeat sensing, when said intrinsic atrial rate indication exceeds said maximum atrial tracking rate, said controlling step including the sub-steps of:

timing a postventricular atrial refractory period following generation of a ventricular pacing pulse, maintaining a record for recent cardiac cycles of which of said intrinsic atrial rate and said maximum atrial tracking rate was greater and whether atrial heartbeat sensing occurred during a postventricular atrial refractory period, deciding whether said record meets a predetermined criterion, and governing whether ventricular pacing pulses are generated in said first or said second mode in accordance with whether said predetermined criterion is met.

37. A method of operating a dual-chamber rate-responsive pacemaker in accordance with claim 36 wherein when a switch is made from said second mode to said first mode, said controlling step temporarily increases the cycle time of the pacemaker.

38. A method of operating a dual-chamber rate-responsive pacemaker in accordance with claim 34 or 36 wherein, when ventricular pacing pulses are generated in synchrony with atrial heartbeat sensing, a pulse is generated after A-V delay interval following atrial heartbeat sensing, and further including the step of adjusting said A-V delay interval to be a function of said metabolic indicator rate.

39. A method of operating a dual-chamber rate-responsive pacemaker, comprising the steps of:

generating ventricular pacing pulses, sensing atrial heartbeats, deriving a metabolic indicator rate, setting at least one atrial refractory period as a function of said metabolic indicator rate, determining whether sensed atrial heartbeats fall within at least one of said atrial refractory periods, and in response to said determining step, controlling a first operating mode in which ventricular pacing pulses are generated in synchrony with sensed atrial heartbeats and a second operating mode in which ventricular pacing pulses are generated at a rate which is a function of said metabolic indicator rate with timing independent of sensed atrial heartbeats.

40. A method of operating a dual-chamber rate-responsive pacemaker in accordance with claim 39 wherein, in said first mode, a ventricular pulse is generated following a sensed atrial heartbeat after an A-V delay interval which is a function of said metabolic indicator rate.

41. A method of operating a dual-chamber rate-responsive pacemaker in accordance with claim 39 wherein said controlling step further includes the sub-steps of:

storing information relating to recent cardiac cycles in which sensed atrial heartbeats fell within said postventricular atrial refractory period but after an A-V delay interval and in which the interval between sensed atrial heartbeats is shorter than said total atrial refractory period, and using the stored information in selecting between said first and second operating modes.

42. A method of operating a dual-chamber rate-responsive pacemaker in accordance with claim 39 wherein a change is made from said first mode to said second mode upon a predetermined percentage of sensed atrial heartbeats falling within said postventricular atrial refractory period but after an A-V delay interval, and a change is made from said second mode to said first mode when the interval between sensed atrial heartbeats in longer than said total atrial refractory period in a predetermined preponderance of the most recent cardiac cycles.

43. A method of operating a dual-chamber rate-responsive pacemaker in accordance with claim 39 wherein said controlling step includes the sub-steps of:

maintaining a record of recent cardiac cycles in which atrial heartbeats fall within said postventricular atrial refractory period but accur at a physiological rate, and governing switches between said first and second operating modes in response to the maintained record satisfying predetermined criteria.

44. A method of operating a dual-chamber rate-responsive pacemaker in accordance with claim 43 wherein when a switch is made from said second mode to said first mode, said controlling step temporarily increases the cycle time of the pacemaker.

45. A method of operating a dual-chamber rate-responsive pacemaker, comprising the steps of:
generating ventricular pacing pulses,
sensing atrial heartbeats,
determining a metabolic indicator rate,
deriving a maximum atrial tracking rate as a function of said metabolic indicator rate,
comparing said maximum atrial tracking rate with the rate of said sensed atrial heartbeats over a plurality of cardiac cycles, and, depending on the pattern of the results of the comparison, classifying whether the atrial heartbeat rate is physiological or pathological, and
keying ventricular pacing pulse generation to atrial heartbeat sensing when the atrial heartbeat rate is physiological, and keying ventricular pacing pulse generation to said metabolic indicator rate independent of atrial heartbeat sensing when the atrial heartbeat rate is pathological.

46. A method of operating a dual-chamber rate-responsive pacemaker in accordance with claim 45 wherein said comparing and classifying step, the highest atrial heartbeat rate which is still classified as physiological in increased as the metabolic indicator rate increases.

47. A method of operating a dual-chamber rate-responsive pacemaker in accordance with claim 46 wherein, when the atrial heartbeat rate is physiological, ventricular pacing pulse generation occurs at a time after atrial heartbeat sensing which decreases as the metabolic indicator rate increases.

48. A method of operating a dual-chamber rate-responsive pacemaker in accordance with claim 47 further including the step of:
generating atrial pacing pulses and sensing ventricular heartbeats; and wherein said keying, when the atrial heartbeat rate is physiological, control DDD pacer operation with the cycles time being a function of said metabolic indicator rate.

49. A method of operating a dual-chamber rate-responsive pacemaker in accordance with claim 48 wherein, on average, the atrial heartbeat rate is classified as pathological in fewer heartbeat cycles than are required to classify the atrial heartbeat rate is physiological.

50. A method of operating a dual-chamber rate-responsive pacemaker in accordance with claim 49 wherein classifying an atrial heartbeat rate as physiological is delayed a length of time which is an increasing function of the length of time during which the previous atrial heartbeat rate was classified as pathological.

51. A method of operating a dual-chamber rate-responsive pacemaker in accordance with claim 50 wherein said comparing and classifying step includes the sub-steps of:
timing a postventricular atrial refractory period ("PVARP"),
determining a total atrial refractory period('-'TARP").
classifying a first atrial heartbeat rate as pathological when a predetermined percentage of atrial heartbeats are sensed during the PVARP,
timing the intervals between successively sensed atrial heartbeats,
classifying a subsequent atrial heartbeat rate as pathological when the atrial heartbeat intervals are shorter than the TARP, and
extending the duration of a pacer cycle in response to a non-pathological rate being determined with a predetermined regularity simultaneously with the atrial heartbeat rate being classified as pathological.

52. A method of operating a dual-chamber rate-responsive pacemaker in accordance with claim 46 further including the steps of:
generating atrial pacing pulses and sensing ventricular heartbeats; and wherein said keying, when the atrial heartbeat rate is physiological, controls DDD pacer operation with the cycle time being a function of said metabolic indicator rate.

53. A method of operating a dual-chamber rate-responsive pacemaker in accordance with claim 46 wherein, on average, the atrial heartbeat rate is classified as pathological in fewer heartbeat cycles than are required to classify the atrial heartbeat rate as physiological.

54. A method of operating a dual-chamber rate-responsive pacemaker in accordance with claim 46 wherein classifying an atrial heartbeat rate as physiological is delayed a length of time which is an increasing function of the length of time during which the previous atrial heartbeat rate was classified as pathological.

55. A method of operating a dual-chamber rate-responsive pacemaker in accordance with claim 46 wherein said comparing and classifying step includes the sub-steps of:
timing a postventricular atrial refractory period ("PVARP"),
determining a total atrial refractory period ("TARP"),
classifying a first atrial heartbeat rate as pathological when a predetermined percentage of atrial heartbeats are sensed during the PVARP,
timing the intervals between successively sensed atrial heartbeats,
classifying a subsequent atrial heartbeat rate as pathological when the atrial heartbeat intervals are shorter than the TARP, and
extending the duration of a pacer cycle in response to a non-pathological rate being determined with a predetermined regularity simultaneously with the atrial heartbeat rate being classified as pathological.

56. A method of operating a dual-chamber rate-responsive pacemaker in accordance with claim 45 wherein, when the atrial heartbeat rate is physiological, ventricular pacing pulse generation occurs at a time after atrial heartbeat sensing which decreases as the metabolic indicator rate increases.

57. A method of operating a dual-chamber rate-responsive pacemaker in accordance with claim 56 further including the steps of:
generating atrial pacing pulses and sensing ventricular heartbeats; and wherein said keying, when the atrial heartbeat rate is physiological, controls DDD pacer operation with the cycle time being a function of said metabolic indicator rate.

58. A method of operating a dual-chamber rate-responsive pacemaker in accordance with claim 45 further including the steps of:

generating atrial pacing pulses and sensing ventricular heartbeats; and wherein said keying, when the atrial heartbeat rate is physiological, controls DDD pacer operation with the cycle time being a function of said metabolic indicator rate.

59. A method of operating a dual-chamber rate-responsive pacemaker in accordance with claim 45 wherein, on average, the atrial heartbeat rate is classified as pathological in fewer heartbeat cycles than are required to classify the atrial heartbeat rate as physiological.

60. A method of operating a dual-chamber rate-responsive pacemaker in accordance with claim 59 wherein classifying an atrial heartbeat rate as physiological is delayed a length of time which is an increasing function of the length of time during which the previous atrial heartbeat rate was classified as pathological.

61. A method of operating a dual-chamber rate-responsive pacemaker in accordance with claim 45 wherein classifying an atrial heartbeat rate as physiological is delayed a lenth of time which is an increasing function of the length of time during which the previous atrial heartbeat rate was classified as pathological.

62. A method of operating a dual-chamber rate-responsive pacemaker in accordance with claim 45 wherein said comparing and classifying step includes the sub-steps of:
    timing a postventricular atrial refractory period ("PVARP"),
    determining a total atrial refractory period ("TARP"),
    classifying a first atrial heartbeat rate as pathological when a predetermined percentage of atrial heartbeats are sensed during the PVARP,
    timing the intervals between successively sensed atrial heartbeats,
    classifying a subsequent atrial heartbeat rate as pathological when the atrial heartbeat intervals are shorter than the TARP, and
    extending the duration of a pacer cycle in response to a non-pathological rate being determined with a predetermined regularity simultaneously with the atrial heartbeat rate being classified as pathological.

63. A method of operating a dual-chamber rate-responsive pacemaker, comprising the steps of:
    generating atrial and ventricular pacing pulses;
    sensing atrial and ventricular heartbeats;
    determining a metabolic indicator rate;
    ascertaining whether sensed atrial heartbeats are occurring at a rate which is pathological for the current metabolic indicator rate; and
    controlling said generating and sensing steps to take place normally in a DDDR mode but to switch to a VVIR mode when the rate of the atrial heartbeats is pathological, said switch between modes being based on the most recent cardiac cycles, with fewer cardiac cycles being necessary to effect a switch from DDDR to VVIR mode then from VVIR to DDDR mode.

64. A method of operating a dual-chamber rate-responsive pacemaker, comprising the steps of:
    generating atrial and ventricular pacing pulses;
    sensing atrial and ventricular heartbeats;
    determining a metabolic indicator rate;
    ascertaining whether sensed atrial heartbeats are occurring at a rate which is pathological for the current metabolic indicator rate;
    controlling said generating and sensing steps to take place normally in a DDDR mode but to switch to a VVIR mode when the rate of the atrial heartbeats is pathological, and
    detecting a PMVVIR condition when the pacemaker is operating in the VVIR mode, and in response thereto controlling a switch from VVIR mode to DDDR mode and temporarily extending the V-A interval in the DDDR mode.

65. A method of operating a dual-chamber rate-responsive pacemaker in accordance with claim 63 or 64 wherein, in said ascertaining step, the highest atrial heartbeat rate which is considered to be non-pathological is an increasing function of the metabolic indicator rate.

66. A method of operating a dual-chamber rate-responsive pacemaker in accordance with claim 65 wherein, in the DDDR mode of opertion, the A-V delay is a decreasing function of the metabolic indicator rate.

67. A dual-chamber rate-responsive pacemaker, comprising:
    means for generating ventricular pacing pulses,
    means for sensing atrial heartbeats,
    sensor means for deriving a metabolic indicator rate,
    means for setting at least one atrial refractory period as a function of said metabolic indicator rate,
    means responsive to said atrial heartbeat sensing means for determining whether sensed atrial heartbeats fall within said at least one atrial refractory period, and
    means reponsive to said determining means for controlling a first operating mode in which said generating means generates ventricular pacing pulses in synchrony with sensed atrial heartbeats and a second operating mode in which said generating means generates ventricular pacing pulses at a rate which is a function of said metabolic indicator rate with timing independent of sensed atrial heartbeats.

68. A dual-chamber rate-responsive pacemaker in accordance with claim 67 wherein said controlling means, when operating in said first mode, controls said ventricular pulse generating means to generate a pulse following a sensed atrial heartbeat after an A-V delay interval which is a function of said metabolic indicator rate.

69. A dual-chamber rate-responsive pacemaker in accordance with claim 67 wherein said controlling means further includes a means for storing information relating to recent cardiac cycles in which sensed atrial heartbeats fell within said at least one atrial refractory period, and wherein said controlling means is further responsive to said storing means.

70. A dual-chamber rate-responsive pacemaker in accordance with claim 67 wherein said controlling means causes a change from said first mode to said second mode upon a predetermined percentage of sensed atrial heartbeats falling within a postventricular atrial refractory period but after an A-V delay interval, and said controlling means causes a change from said second mode to said first mode when the interval between sensed atrial heartbeats is longer than a total atrial refractory period in a predetermined preponderance of the most recent cardiac cycles.

71. A dual-chamber rate-responsive pacemaker in accordance with claim 79 wherein said controlling means includes:

means for maintaining a record of recent cardiac cycles in which atrial heartbeats fall within said at least one atrial refractory period but occur at a physiological rate, and means responsive to said record maintaining means satisfying predetermined criteria for governing switches between said first and second operating modes.

72. A dual-chamber rate-responsive pacemaker in accordance with claim 71 wherein when said governing means causes a switch from said second mode to said first mode, said controlling means temporarily increases the cycle time of the pacemaker.

73. A method of operating a dual-chamber rate-responsive pacemaker, comprising the steps of:
generating ventricular pacing pulses,
sensing atrial heartbeats,
deriving a metabolic indicator rate,
setting at least one atrial refractory period as a function of said metabolic indicator rate,
determining whether sensed atrial heartbeats fall within said at least one atrial refractory period, and
in response to said determining step, controlling a first operating mode in which ventricular pacing pulses are generated in synchrony with sensed atrial heartbeats and a second operating mode in which ventricular pacing pulses are generated at a rate which is a function of said metabolic indicator rate with timing independent of sensed atrial heartbeats.

74. A method of operating a dual-chamber rate-responsive pacemaker in accordance with claim 73 wherein, in said first mode, a ventricular pulse is generated following a sensed atrial heartbeat after an A-V delay interval which is a function of said metabolic indicator rate.

75. A method of operating a dual-chamber rate-responsive pacemaker in accordance with claim 73 wherein said controlling step further includes the sub-steps of:
storing information relating to recent cardiac cycles in which sensed atrial heartbeats fell within said at least one atrial refractory period, and
using the stored information in selecting between said first and second operating modes.

76. A method of operating a dual-chamber rate-responsive pacemaker in accordance with claim 73 wherein a change is made from said first mode to said second mode upon a predetermined percentage of sensed atrial heartbeats falling within a postventricular atrial refractory period but after an A-V delay interval, and a change is made from said second mode to said first mode when the interval between sensed atrial heartbeats is longer than a total atrial refractory period in a predetermined preponderance of the most recent cardiac cycles.

77. A method of operating a dual-chamber rate-responsive pacemaker in accordance with claim 73 wherein said controlling step includes the sub-steps of:
maintaining a record of recent cardiac cycles in which atrial heartbeats fall within said at least one atrial refractory period but occur at a physiological rate, and
governing switches between said first and second operating modes in response to the maintained record satisfying predetermined criteria.

78. A method of operating a dual-chamber rate-responsive pacemaker in accordance with claim 77 wherein when a switch is made from said second mode to said first mode, said controlling step temporarily increases the cycle time of the pacemaker.

* * * * *